US012186432B2

(12) United States Patent
Liu et al.

(10) Patent No.: US 12,186,432 B2
(45) Date of Patent: *Jan. 7, 2025

(54) PREPARATION METHOD OF SUSTAINED-RELEASE MICROPARTICLES (71) Applicant: AC PHARMACEUTICALS CO., LTD., Guangzhou (CN)

(72) Inventors: Feng Liu, Guangzhou (CN); Shuting Lai, Guangzhou (CN); Yang Zheng, Guangzhou (CN); Fuchun Cao, Guangzhou (CN); Yuanfa Lian, Guangzhou (CN)

(73) Assignee: AC PHARMACEUTICALS CO., LTD., Guangzhou (CN)

( * ) Notice: Subject to any disclaimer, the term of this patent is extended or adjusted under 35 U.S.C. 154(b) by 55 days.

This patent is subject to a terminal disclaimer.

(21) Appl. No.: 17/165,690

(22) Filed: Feb. 2, 2021

(65) Prior Publication Data

US 2021/0154147 A1 May 27, 2021

Related U.S. Application Data (63) Continuation-in-part of application No. 16/095,315, filed as application No. PCT/CN2017/081640 on Apr. 24, 2017.

(30) Foreign Application Priority Data

Apr. 26, 2016 (CN) .......................... 201610269834.1

(51) Int. Cl.
*A61K 9/50* (2006.01)
(52) U.S. Cl.
CPC .......... *A61K 9/5089* (2013.01); *A61K 9/5015* (2013.01); *A61K 9/5031* (2013.01); *A61K 9/5036* (2013.01)
(58) Field of Classification Search
CPC .................................................. A61K 9/5089
See application file for complete search history.

(56) References Cited

U.S. PATENT DOCUMENTS

| | | | | |
|---|---|---|---|---|
| 5,556,642 A * | 9/1996 | Kobayashi | ............. | A61K 9/146 514/963 |
| 6,902,743 B1 * | 6/2005 | Setterstrom | .......... | A61K 9/5026 424/490 |
| 2002/0198315 A1 * | 12/2002 | Hutchinson | .......... | A61K 47/593 524/832 |
| 2008/0131513 A1 * | 6/2008 | Woo | ...................... | A61K 47/183 514/17.5 |
| 2010/0316571 A1 * | 12/2010 | Simone | ................ | A61K 9/1075 977/773 |

FOREIGN PATENT DOCUMENTS

CN 105963258 A * 9/2016 ............. A61K 38/08

OTHER PUBLICATIONS

Weidner, Drug Delivery Today, 7, 11, 2002 (Year: 2002).*
Berkland, Journal of Controlled Release, 82, 2002 (Year: 2002).*

* cited by examiner

*Primary Examiner* — Robert A Wax
*Assistant Examiner* — William Craigo
(74) *Attorney, Agent, or Firm* — CBM PATENT CONSULTING, LLC (57) ABSTRACT

In the present invention, the whole preparation process of the sustained-release microparticles is at normal or low temperature, which is highly advantageous for the preparation of a polymer-based composition from a high-temperature-sensitive drug, particularly a protein, nucleic acid and peptide drug, and the bioactivity of the active substance can be maintained to the greatest extent throughout the process compared to the disclosed technology; at the same time, the prepared sustained-release microparticles have an excellent sustained-release effect close to zero order, and the drug concentration is stabilized during the release, which overcomes the defects that the microparticles obtained by the conventional S/O/W process of pre-preparing the drug microparticles have no drug release in the earlier stage and a rapid release of the drug in the later stage; and in addition, the sustained-release microparticles have higher drug loading rate and drug encapsulation rate.

2 Claims, 1 Drawing Sheet

PREPARATION METHOD OF SUSTAINED-RELEASE MICROPARTICLES

This application is a continuation in part of application U.S. Ser. No. 16/095,315 that claims the U.S. national phase of International Application No. PCT/CN2017/081640 Filed on 24 Apr. 2017 which designated the U.S. and claims priority to Chinese Application No. CN201610269834.1 filed on 26 Apr. 2016, the entire contents of each of which are hereby incorporated by reference.

TECHNICAL FIELD

The present invention relates to a method of encapsulating a water-soluble drug, particularly a protein, nucleic acid or peptide drug, in a biodegradable and biocompatible polymer to obtain sustained-release microparticles capable of sustained-releasing the drug.

BACKGROUND ART

In recent years, a large number of bioactive substances, such as oligopeptides, polypeptides and proteins, have received much attention as drug candidates, and they play an important role in the treatment of severe symptoms (cancer, anemia, multiple sclerosis, hepatitis, etc.). However, these macromolecular active substances are relatively fragile because of their poor stability in the gastrointestinal tract (easily degraded at low pH or proteolysis), short circulating half-lives, and poor permeability through the intestinal wall, so they have very low bioavailability and thus are difficult to administer orally. Administration by injection or parenteral route is still the preferred route of administration for active substances such as polypeptides and proteins. Many preparations of peptides and proteins that can be injected by intravenous, intramuscular or subcutaneous routes have been marketed or under development, such as leuprorelin sustained-release microparticles, goserelin sustained-release implants, triptorelin sustained-release microparticles, etc.

For many peptide agents, particularly hormones, which require long-term continuous administration at a controlled rate, the systemic concentrations required for these active substances to produce the desired effect on the target tissue or organ are high, and therefore, it is necessary to obtain the concentration required in the therapeutic window by frequently injecting high doses, which often results in systemic toxicity that is detrimental to the patient. At the same time, the injection administration is painful, and therefore, patient's compliance is low, the curative effect is poor, and the side effects are large. These problems can be solved by a drug delivery system (DDS) of polymer-based active substances. According to the system, the active ingredient is encapsulated in a biodegradable and biocompatible polymer matrix to form a microcapsule, a microparticle or a transplantable rod, so that the active ingredient is released stably for a long period of time, thereby achieving the purpose of sustained release and controlled release.

A variety of microparticle preparation methods have been reported, such as solvent evaporation, coacervation, spray drying, spray freeze drying and the like. The most used one is the solvent evaporation in an aqueous phase, which can be subdivided into a single emulsion method (Oil/Water, 0/W; Water/Oil, W/O) and a double emulsion method (Water/Oil/Water, W/O/W; Water/Oil/Oil, W/O/O).

An improved double emulsion method (such as CN102245210 A, CN1826170 B) comprises: directly suspending polypeptide powder in an organic phase to form a solid/oil (S/O) suspension, and then dispersing the suspension into an aqueous phase to form an S/O/W double emulsion. Since the polypeptide powder is generally insoluble in the intermediate organic phase solvent, this method can avoid the diffusion of the internal aqueous phase to the external aqueous phase in the $W_1/O/W_2$ double emulsion method, thereby increasing the encapsulation rate.

In the S/O/W method, the size of the pre-prepared active substance particles is very important. When the diameter of the solid protein particles is increased from 5 micrometers to 20 micrometers, not only the initial release rate is doubled, but also the microencapsulation rate is reduced from 80% to 20%. The generally obtained protein and polypeptide freeze-dried powder has an average particle size of 10 to 1000 μm. For example, the typical protein and polypeptide freeze-dried powder has an average particle size of about 10 to 500 μm. If powder having such a large particle size is directly suspended in an organic solvent to form an S/O suspension and then the S/O/W double emulsion method is used to prepare the microparticles, the drug will not be encapsulated highly, so that the encapsulation rate is low, or the sustained-release effect is not satisfactory (the burst release of the drug in the earlier stage is large, but the drug release in the later stage is insufficient), or the prepared microparticles have too large particle size to be administered; and at the same time, the shape of the drug powder also affects the shape of the microparticles. Therefore, it is generally necessary to reduce the average particle size of the drug powder to 1-10 μm in advance, and then use this powder for an S/O/W double emulsion method to prepare sustained-release particles (U.S. Pat. No. 6,270,700; Takada S, et al. Journal of Controlled Release. 2003, 88(2): 229-42).

However, the preparation of small-particle-size drugs is often carried out by grinding, spray drying, ultrasonic pulverization, jet pulverization, crystallization, etc. (such as CN1494900 B), the process is complicated, and it easily causes the active substances to be deactivated. Grinding is limited by dust, heavy metal contamination and protein denaturation caused heat of grinding; spray drying may provide small enough protein particles, but high shear forces near the nozzle and interfacial tension between liquid and air can denature proteins. In addition, surfactants must be used in spray drying or spray freeze drying, which in turn cause the protein to interact with the solvent in the next formulation procedure. At the same time, if the complexity of the particle preparation process is reduced and the particle size is sacrificed to ensure the activity of the drug, the particle size of the prepared particles is slightly smaller than that of the microparticles (i.e., the particle radius is much larger than the thickness of the polymer layer), and there will be cases where each microparticle only wraps one or a few active substance particles, resulting in very little drug release in the early stage and quick release of the drug in the later stage, so the sustained release effect is not achieved.

Another improved double emulsion method (such as CN102233129 B, CN102871969 A, CN101721375 B, CN102885785 B, etc.) comprises: preparing small particles from the active substance and one or more additives (such as glucan, polyethylene glycol, sodium alginate, etc.), and then washing away some or all of the additives with an organic solvent to obtain porous semi-hollowed or hollowed active substance small particles, and preparing microparticles by a conventional S/O/W process. According to this method, a more complicated step of the preparation of small particles is added, and an organic solvent is required to remove the additives therein. Moreover, most of these additives are water-soluble substances. If they are not completely removed, they may easily affect the release effect, accelerate the release of active substances, or form gels (such as high-molecular-weight glucan, sodium alginate), which may cause microparticle breakage, delayed drug release, or incomplete release. In US20080131513, a buffering agent capable of resisting a change of a pH is formed by using basic amino acid and acetic acid, so as to reduce an interaction between an active agent and a biodegradable polymer, but the sustained-release mechanism of PLGA microspheres is implemented through drug diffusion and polyester degradation. Moreover, an acidic microenvironment generated by the degradation product of PLGA may make PLGA degradation faster than that under a neutral condition, which is also a key factor to maintain the drug release at a certain rate. If the microenvironment of the microspheres is maintained unchanged, which means that the pH value in a physiological environment is maintained (the pH is about 7), the degradation rate of PLga can be greatly reduced, but it is not beneficial for maintaining a certain drug release rate.

According to a further optimized preparation method (U.S. Pat. No. 5,556,642), the water-soluble active substance and the polymer are dissolved in a cosolvent, and then the organic solvent is removed by evaporation to obtain a solid mixture, then the solid mixture is dissolved in an organic solvent, and the microparticles are prepared by an O/W method. This method overcomes the defects of no drug release in the early stage and the rapid release of the drug in the later stage in the traditional S/O/W method. However, the process of preparing a solid by volatilizing an organic solvent is not beneficial to temperature-sensitive active substances, and it easily causes denaturation. If the organic solvent is volatilized at a lower temperature, the active substance will accumulate and precipitate during solidification due to the slow volatilization of the solvent, and the active substance in the dried solid dispersion will also exist in a large volume, such as a block, a band or a thread, causing difficulties or waste to the subsequent process of preparing the microparticles, and also leading to unstable release.

In U.S. Pat. No. 6,235,224B1, a solution of a drug and a polymer is precipitated in an anti-solvent to form nanospheres or microspheres by the anti-solvent method, but the microspheres prepared by the method have a very short release time, such as nanospheres composed of PLA and polyfumaric acid by the method for releasing insulin: about 24% of total insulin is released 1 hour later; and nearly 45% of drug is released from the nanospheres 5 hours later. Therefore, sustained-release microspheres capable of being released for several weeks or months cannot be prepared by the method.

In US20020198315A1, peptide/polyester salt is prepared from a solution of acetate of a basic peptide and PLGA of a terminal carboxyl group by an instantaneous method, such as spray drying or liquid nitrogen extraction, and then freeze drying is carried out for 24 hours to remove acetic acid, so as to dissolve a polypeptide in a polymer solution and accelerate drug release. However, the salt is not beneficial for encapsulating a polypeptide drug due to its property as well as a surfactant, because in a process of preparing the microspheres by O/W or S/O/W emulsification method, an outermost layer of emulsion droplets formed by an organic solvent solution of the salt in an external water phase is a rich hydrophilic polypeptide layer, followed by a hydrophobic PLGA layer, and a large number of polypeptides may be dissolved into the water phase, resulting in a great decrease in a drug encapsulation efficiency. Even after administration, a large number of polypeptides on the surface of the microspheres may cause initial burst release, and a PLGA shell on a next layer may cause slow release or even no release of the drug in a next period of time. Meanwhile, the patent considers that the peptide/polyester salt cannot be formed by simply mixing the polypeptide with the PLGA of the terminal carboxyl group.

SUMMARY OF THE INVENTION

The objective of the present invention is to overcome the defects in the prior arts and to provide a method for preparing sustained-release microparticles by emulsion-solvent volatilization without preparing small-particle-size drug powder in advance, and the process is relatively simple, can maintain the bioactivity of the active substance, and has a high encapsulation rate and an excellent sustained-release effect.

In order to achieve the objective, the present invention adopts the following technical solution: a preparation method of sustained-release microparticles comprises the following steps:
1) preparing a solid dispersion of a water-soluble drug and a biodegradable and biocompatible poorly water-soluble polymer;
2) dissolving the solid dispersion prepared in step 1) in an organic solvent C to form a solid dispersion emulsion (internal oil phase), the organic solvent C being an organic solvent which is not capable of dissolving the water-soluble drug but capable of dissolving the poorly water-soluble polymer, has a boiling point lower than that of water and is insoluble or poorly soluble in water;
3) adding the solid dispersion emulsion obtained in step 2) into an surfactant-containing aqueous solution (external aqueous phase) to form a uniform emulsion; and
4) solidifying microparticles in the emulsion by solvent volatilization or solvent extraction, collecting the microparticles, washing with ultrapure water several times to remove the surfactant attached to the surface of the microparticles, and drying to obtain the sustained-release microparticles.

The water-soluble drug includes at least one of a basic substance or a basic-group-containing substance (such as an alkaloid, a short peptide, an antagonist, an antibiotic, a small molecule nucleic acid) and salts thereof having a molecular weight of less than about 3350 Da, and a basic substance or a basic-group-containing substance (such as a polypeptide, a protein, a nucleic acid, an antibody, an antigen, an antibiotic, etc.) and salts thereof having a molecular weight of more than about 3350 Da. Preferably, the water-soluble drug is at least one of a protein drug, a peptide drug and a nucleic acid drug. Preferably, the water-soluble drug has a molecular weight of less than about 3350 Da.

The protein includes a natural, synthetic, semi-synthetic or recombinant compound or protein, or a basic structure containing an α amino acid covalently linked by a peptide bond, or is functionally related. Specifically, the protein includes, but is not limited to, at least one of globular proteins (such as albumin, globulin, and histone), fibrin (such as collagen, elastin, and keratin), compound proteins (which may contain one or more non-peptide components, such as glycoproteins, nucleoproteins, mucoproteins, lipoproteins, and metalloproteins), therapeutic proteins, fusion proteins, receptors, antigens (such as synthetic or recombinant antigens), viral surface proteins, hormones and hormone analogs, antibodies (such as monoclonal or polyclonal antibodies), enzymes, Fab fragments, interleukins and derivatives thereof, and interferons and derivatives thereof.

The nucleic acid is a compound that is natural, synthetic, or semi-synthetic, or an at least partially recombined compound formed from two or more identical or different nucleotides, and may be single-stranded or double-stranded. Non-limiting examples of nucleic acids include oligonucleotides, antisense oligonucleotides, aptamers, polynucleotides, deoxyribonucleic acids, siRNAs, nucleotide constructs, single- or double-stranded segments, and precursors and derivatives thereof (such as glycosylated, hyperglycosylated, PEGylated, FITC-labeled, nucleosides, and salts thereof). Specifically, the nucleic acid includes, but is not limited to, at least one of Mipomersen, Alicaforsen, Nusinersen, Volanesorsen, Custirsen, Apatorsen, Plazomicin, RG-012, RG-101, ATL1102, ATL1103, IONIS-HBV$_{Rx}$, IONIS-HBV-L$_{Rx}$, IONIS-GCGR$_{Rx}$, IONIS-GCCR$_{Rx}$, IONIS-HTT$_{Rx}$, IONIS-TTR$_{Rx}$, IONIS-PKK$_{Rx}$, IONIS-APO (a)-L$_{Rx}$, IONIS-ANGPTL3-$_{LRx}$, IONIS-AR-2.5$_{Rx}$, IONIS-DMPK-2.5$_{Rx}$, IONIS-STAT3-2.5$_{Rx}$, IONIS-SOD1$_{Rx}$, IONIS-GSK4-L$_{Rx}$, IONIS-PTP1B$_{Rx}$, IONIS-FGFR$_{4Rx}$, and IONIS-DGAT2$_{Rx}$. The above nouns are names or codes of the nucleic acid drugs.

Preferably, the water-soluble drug preferably contains a water-soluble substance (such as a peptide drug) containing at least one basic amino group, including, but not limited to, at least one of adrenocorticotropic hormone (ACTH) and derivatives thereof, epidermal growth factor (EGF), platelet-derived growth factor (TOGF), gonadotropin releasing hormone (LHRH) and derivatives or analogs thereof, calcitonin, insulin-like growth factors (IGF-I, IGF-II), cell growth factors (such as EGF, TGF-α, TGF-β, PDGF, FGF hydrochloride, basic FGF, etc.), glucagon-like peptides (such as GLP-1, GLP-2) and derivatives or analogs thereof, neurotrophic factors (such as NT-3, NT-4, CNTF, GDNF, BDNF, etc.), colony stimulating factors (such as CSF, GCSF, GMCSF, MCSF, etc.), and their synthetic analogs, modifications and drug active fragments. The derivatives or analogs of GLP-1 include, but are not limited to, exendin-3 and exendin-4.

The water-soluble drug containing at least one basic amino group is preferably at least one of a peptide substance and derivatives or analogs thereof, and the peptide substance includes, but is not limited to, glucagon (29-amino-acid peptide), sermorelin (29-amino-acid peptide), aviptadil (28-amino-acid peptide), secretin (27-amino-acid peptide), ziconotide (25-amino-acid peptide), cosyntropin (24-amino-acid peptide), bivalirudin (20-amino-acid peptide), somatostatin (14-amino-acid peptide), terlipressin (12-amino-acid peptide), goserelin (10-amino-acid peptide), triptorelin (10-amino-acid peptide), nafarelin (10-amino-acid peptide), gonadorelin (10-amino-acid peptide), cetrorelix (10-amino-acid peptide), degarelix (10-amino-acid peptide), antide (10-amino-acid peptide), angiotensin (6-10-amino-acid peptide), leuprorelin (9-amino-acid peptide), alarelin (9-amino-acid peptide), buserelin (9-amino-acid peptide), deslorelin (9-amino-acid peptide), octreotide (8-amino-acid peptide), lanreotide (8-amino-acid peptide), bremelanotide (7-amino-acid peptide), eptifibatide (7-amino-acid peptide), hexarelin (6-amino-acid peptide), splenopentin (5-amino-acid peptide), thymopentin (5-amino-acid peptide), elcatonin (31-amino-acid peptide), semaglutide (31-amino-acid peptide)), glucagon-like peptide-1 (31-amino-acid peptide), liraglutide (34-amino-acid peptide), teriparatide (34-amino-acid peptide), pramlintide (37-amino-acid peptide), enfuvirtide (38-amino-acid peptide), exenatide (39-amino-acid peptide), adrenocorticotropic hormone (39-amino-acid peptide), corticotropin releasing hormone (41-amino-acid peptide), tesamorelin (44-amino-acid peptide), lixisenatide (44-amino-acid peptide), follicle stimulating hormone (118-amino-acid peptide), dulaglutide (274-amino-acid peptide) and albiglutide (645-amino-acid peptide).

The peptide substance is preferably a short peptide or polypeptide having not more than 30 amino acid residues. The derivative or analog of the peptide substance refers to a product of at least one of polypeptides having not more than 30 amino acid residues and variants or analogs thereof modified by a water-soluble or poorly water-soluble group or substance, and has higher biological and pharmacological activity and stability, or has new functions or attributes.

The derivative or analog of the peptide drug includes at least one of glucagon-like peptides (such as GLP-1, GLP-2) and derivatives or analogs thereof, including, but not limited to at least one of exendin-3, exendin-4, and variants or analogs thereof.

The variants or analogs refer to peptides in which the amino acid sequence varies due to substitution (or replacement), deletion, insertion, fusion, truncation or any combination thereof of one or more amino acid residues, and the variant polypeptides may be fully functional or may lack one or more functions. For example, the second position of the analog exendin-4 of glucagon-like peptide-1 (GLP-1) is glycine while the second position of GLP-1 is alanine, and the exendin-4 is capable of binding to a GLP-1 receptor and producing signal cascade transduction.

The water-soluble or poorly water-soluble group or substance is selected from at least one of polyethylene glycol and derivatives thereof, cyclodextrins, hyaluronic acid, short peptides, albumin, amino acid sequences, nucleic acids, genes, antibodies, phosphoric acid, sulfonic acid, fluorescent dyes, KLH, OVA, PVP, PEO, PVA, alkanes, aromatic hydrocarbons, biotin, immunoglobulin, albumin, polyamino acids, gelatin, succinylated gelatin, acrylamide derivatives, fatty acids, polysaccharides, lipid amino acids, chitosan and glucan, preferably polyethylene glycol and/or derivatives thereof, and the structure of the polyethylene glycol and derivatives thereof may be branched, linear, bifurcated or dumbbell-shaped. The derivatives of polyethylene glycol include, but are not limited to, monomethoxy polyethylene glycol and methoxy polyethylene glycol propionate. The polyethylene glycol and derivatives thereof are either commercially available or can be prepared by those skilled in the art through techniques well known to them.

The water-soluble or poorly water-soluble substance is modified to be a modifying agent with an activating group and coupled to the peptide substance derivative, and the activating group is selected from at least one of maleimide, halogen, vinyl sulfone, disulfide bond, sulfhydryl group, aldehyde group, carbonyl group, 0-substituted hydroxylamine, active ester, alkenyl group, alkynyl group, azide group and other groups having high chemical reactivity. Preferably, the activating group is selected from at least one of maleimide, halogen, vinyl sulfone and disulfide bond; more preferably maleimide and/or disulfide bond. The number of activating groups carried on the polymer is one or more, and when the number of activating groups is more than one, the activating groups may be identical or different.

The molecular weight of the one or more water-soluble or poorly water-soluble substances is 1-60 kDa, preferably 2-50 kDa, more preferably 5-40 kDa.

The modifying agent having an activating group may be coupled to the peptide or a variant or analog thereof by an amino group, a carboxyl group, a hydroxyl group or a sulfhydryl group on the amino acid sequence. Such a group is typically at the N-terminus, C-terminus, side chain or any site of any amino acid of amino acid residues, such as Lys (lysine), Asp (aspartic acid), Glu (glutamic acid), Cys (cysteine), His (histidine), 4-mercapto proline, Trp (tryptophan), Arg (arginine), Ala (alanine), Gly (glycine), Ser (serine) or Thr (threonine), or derivatives thereof, preferably a site containing a sulfhydryl group. For example, in exendin-4 and analogs thereof, any cysteine residue site or other amino acid residue at 2, 14, 21, 25, 28, 35, 38 or any position is replaced with a cysteine residue site.

Modifications of the peptide and variants or analogs thereof are random modifications, site-directed modifications (specific modifications), single-site modifications or multi-site modifications, preferably single-site-directed modifications.

The peptide and variants or analogs thereof are prepared by a conventional polypeptide synthesis method, including a solid phase polypeptide synthesis method, a liquid phase polypeptide synthesis method, a solid phase-liquid phase polypeptide synthesis method and a recombination method; the reaction between the peptide and variants or analogs thereof and the modifying agent is carried out in an aqueous solution or a buffer salt solution while properly controlling the pH value of the reaction system and monitoring the modified product by HPLC, GPC, etc., the modified product is separated and purified by ion exchange, gel chromatography, etc., and concentration and freeze drying are carried out to obtain the target product.

Preferably, the water-soluble drug in step 1) is of at least one of a free form and a pharmaceutically acceptable salt form. The salt-forming acid may be selected from inorganic acids or organic acids. The inorganic acids include hydrochloric acid, sulfuric acid, phosphoric acid; and the organic acids include acetic acid, formic acid, propionic acid, lactic acid, trifluoroacetic acid, citric acid, fumaric acid, malonic acid, maleic acid, tartaric acid, aspartic acid, benzoic acid, methanesulfonic acid, benzenesulfonic acid, citric acid, malic acid, oxalic acid, succinic acid and carbonic acid, preferably hydrochloric acid, acetic acid, fumaric acid, maleic acid, more preferably acetic acid.

Preferably, the poorly water-soluble polymer in step 1) includes at least one of polyesters, polycarbonates, polyacetals, polyanhydrides, polyhydroxy fatty acids, and copolymers or blends thereof. In detail, the biodegradable and biocompatible polymer is polylactide (PLA), polyglycolide (PGA), lactide-glycolide copolymer (PLGA) and copolymers thereof with polycaprolactone (PCL) or polyethylene glycol (PEG) (such as PLA-PEG, PLGA-PEG, PLGA-PEG-PLGA, PLA-PEG-PLA, PEG-PCL, PCL-PLA-PCL, PCL-PLGA-PCL, PEG-PLA-PEG, PEG-PLGA-PEG), polycaprolactone and copolymer thereof with polyethylene glycol, polyhydroxybutyric acid, polyhydroxyvaleric acid, poly(p-dioxanone) (PPDO), collagen, chitosan, alginic acid and salts thereof, polycyanoacrylates, fibrin, polyanhydrides, polyorthoesters, polyamides, polyphosphazenes, polyphosphates, and copolymers and/or mixtures thereof; preferably PLA, PLGA and their copolymers with polycaprolactone or polyethylene glycol, and mixtures thereof; more preferably PLA, PLGA or mixtures thereof.

The PLA, PLGA and copolymers thereof with PCL or PEG have a weight average molecular weight of 25000-150000 Da, preferably a molecular weight of 30000-130000 Da, more preferably a molecular weight of 35000-110000 Da. The weight average molecular weight used in the present specification is a value obtained by gel permeation chromatography (GPC) measurement.

Alternatively, the PLA, PLGA and copolymers thereof with PCL or PEG (test conditions being −0.5% (w/v), $CHCl_3$, 25° C.) have a viscosity of 0.22-1.1 dL/g, preferably 0.27-1.0 dL/g, more preferably 0.31-0.9 dL/g.

The molecular chains of the poorly water-soluble polymer may carry anionic or cationic groups or may not carry these groups. Preferably, the polymer has a terminal hydroxyl group, a terminal carboxyl group or a terminal ester group, more preferably a polymer having a terminal carboxyl group.

In the PLA, PLGA and copolymers thereof with PCL or PEG, the ratio of lactide to glycolide is from 100:0 to 50:50, preferably from about 90:10 to 50:50, more preferably from 85:15 to 50:50.

In the present invention, the poorly water-soluble polymer for preparing the sustained-release microparticles may be a single polymer or a mixture of multiple polymers, for example, a combination of PLGAs having the same ratio of lactide to glycolide, the same molecular weight and different carried groups, a combination of PLGAs having the same ratio of lactide to glycolide, the same carried group and different molecular weights, a combination of PLGAs having the same molecular weight, the same carried group and different ratios of lactide to glycolide, a combination of PLGAs having different molecular weights, different carried groups and different ratios of lactide to glycolide, a combination of PLGA and PLA, etc.

Preferably, step 1) is carried out by the following steps:
11) completely dissolving the biodegradable and biocompatible poorly water-soluble polymer and the water-soluble drug in an organic solvent A to form a mixed solution of the drug and the polymer; and
12) adding the mixed solution into an organic solvent B or adding the organic solution B into the mixed solution to produce a uniform and fine precipitate, collecting the precipitate, washing the precipitate with the organic solvent B several times, and removing the organic solvent B to obtain a solid dispersion of the water-soluble drug and the poorly water-soluble polymer, wherein the organic solvent B is incapable of dissolving the poorly water-soluble polymer and the water-soluble drug.

The organic solvent A in step 11) is capable of simultaneously dissolving the water-soluble drug and the biodegradable and biocompatible poorly water-soluble polymer. Preferably, the organic solvent A is selected from at least one of glacial acetic acid, acetonitrile, trifluoroacetic acid and dimethyl sulfoxide, more preferably glacial acetic acid or acetonitrile, most preferably glacial acetic acid. The type and proportion of the organic solvent A in the polymer solution are different according to different drugs and polymers, and can be formulated according to actual conditions.

The organic solvent B in step 12) is neither capable of dissolving the water-soluble drug, nor capable of dissolving the biodegradable and biocompatible poorly water-soluble polymer. Preferably, the organic solvent B is selected from at least one of anhydrous diethyl ether, hexane and n-heptane, more preferably anhydrous diethyl ether or hexane (including cyclohexane, n-hexane), most preferably anhydrous diethyl ether. The type and proportion of the organic solvent B in the mixed solution are different according to different drugs and polymers, and can be formulated according to actual conditions.

The organic solvent A is controlled to be at normal temperature or below or at low temperature, and the normal temperature is generally maintained to be 20° C., preferably 10-15° C.; the low temperature is generally maintained to be 10° C. or below, preferably 4-6° C. or below; the organic solvent B is controlled to be at low temperature, and the low temperature is generally maintained to be 15° C. or below, preferably 10° C. or below, more preferably 6° C. or below; and the organic solvent A is 0-10° C., preferably 3-8° C., higher than the temperature of the organic solvent B.

The concentration of the water-insoluble polymer in the organic solvent A varies according to the type and weight average molecular weight of the polymer and the type of the organic solvent. Generally, the mass concentration (polymer mass/organic solvent mass*100%) is 1-18% (w/w), preferably 2-15% (w/w), more preferably 3-12% (w/w).

Preferably, in the solid dispersion, the mass ratio of the water-soluble drug to the poorly water-soluble polymer is 1:1 to 1:99. More preferably, in the solid dispersion, the mass ratio of the water-soluble drug to the poorly water-soluble polymer is 2:3 to 3:97, and more preferably, in the solid dispersion, the mass ratio of the water-soluble drug to the poorly water-soluble polymer is 7:13 to 1:19.

Preferably, the step of removing the organic solvent B does not include a temperature rising process, the step is performed below normal temperature or at low temperature, the normal temperature is generally maintained to be 20-30° C., preferably 20-25° C.; and the low temperature is generally maintained to be 15° C. or below, preferably 10° C. or below. Methods of removing the organic solvent B include, but are not limited to, vacuum drying, freeze drying and fluidized drying.

The organic solvent C is incapable of dissolving the water-soluble drug, but capable of dissolving the biodegradable and biocompatible water-insoluble polymer, has a boiling point lower than that of water and is insoluble or poorly soluble in water. The organic solvent C may be a single organic solvent or two or more miscible organic solvents. The organic solvent C is selected from at least one of aliphatic hydrocarbons (the molecular structure is linear, branched or cyclic, such as n-hexane, n-heptane, n-pentane, cyclohexane, petroleum ether, etc.), halogenated hydrocarbons (such as dichloromethane, chloroform, ethyl chloride, tetrachloroethylene, trichloroethylene, dichloroethane, trichloroethane, carbon tetrachloride, fluorocarbons, chlorobenzene (mono-, di-, trisubstituted), trichlorofluoromethane, etc.), fatty acid esters (such as ethyl acetate, butyl acetate, etc.), aromatic hydrocarbons (such as benzene, toluene, xylene, etc.) and ethers (such as diethyl ether, diisopropyl ether, methyl isobutyl ether, methyl tert-butyl ether, methoxylated ether, alkyl ether, dihaloether, trihaloether, cyclic ether, crown ether, etc.), preferably a halogenated aliphatic hydrocarbon solvent, more preferably dichloromethane and chloroform. The type and proportion of the organic solvent C in the internal oil phase are different according to different drugs and polymers, and are formulated according to actual conditions.

The organic solvent having a boiling point lower than that of water and insoluble or poorly soluble in water is an organic solvent, which is only miscible with water in a volume ratio of <5% and has a lower boiling point (less than or much less than 100° C.) so that it is easily removed by, for example, freeze drying, evaporation or blasting.

The concentration of the poorly water-soluble polymer in the organic solvent C varies according to the type and weight average molecular weight of the polymer and the type of the organic solvent; and generally, the mass concentration (polymer mass/organic solvent mass*100%) is about 1-18% (w/w), preferably about 2-15% (w/w), more preferably about 3-12% (w/w).

The internal oil phase is at lower temperature, the lower temperature may be maintained to be 20° C. or below, preferably 15° C. or below, more preferably 10° C. or below.

The surfactant (or stabilizer)-containing aqueous solution (external aqueous phase) in step 3) is at low temperature, and the low temperature may be maintained to be 12° C. or below, preferably 9° C. or below, more preferably 6° C. or below.

Preferably, the surfactant (or stabilizer) in step 3) is at least one of anionic surfactants, cationic surfactants, zwitterionic surfactants, nonionic surfactants and surface active biomolecules; preferably, the surfactant in step 3) is at least one of anionic surfactants, nonionic surfactants and surface active biomolecules; more preferably, the surfactant in step 3) is at least one of nonionic surfactants and surface active biomolecules. The surfactant can increase the wetting property of the organic phase, improve the stability and shape of the small liquid drop formed during the emulsification process, avoid re-fusion of the small liquid drop, and reduce the number of unencapsulated or partially encapsulated small spherical particles, thereby avoiding initial burst release of microparticles during release.

The cationic surfactants include, but are not limited to, quaternary ammonium compounds such as benzalkonium chloride, cetyltrimethylammonium bromide, lauryl dimethylbenzylammonium chloride, acylcarnitine hydrochloride or alkylpyridine halide.

The anionic surfactants include, but are not limited to, alkyl sulfates such as sodium lauryl sulfate, ammonium lauryl sulfate, sodium stearyl sulfate, etc., potassium laurate, sodium alginate, sodium polyacrylate and derivatives thereof, alkyl polyethylene oxide sulfate, sodium dioctyl sulfosuccinate, sodium carboxymethyl cellulose, sodium oleate, sodium stearate, and sodium salts of cholic acid and other bile acids (such as cholic acid, deoxycholic acid, glycocholic acid, taurocholic acid and glycodesoxycholic acid).

The nonionic surfactants include, but are not limited to, polyoxyethylene fatty alcohol ether (Brij), polysorbates (such as Tween 80, Tween 60), polyoxyethylene fatty acid esters (OEO), polyoxyethylene castor oil derivatives, polyoxyethylene polypropylene glycol copolymer, sucrose fatty acid ester, polyethylene glycol fatty acid ester, polyoxyethylene sorbitan mono-fatty acid ester, polyoxyethylene sorbitan difatty acid ester, polyoxyethylene glycerol mono-fatty acid ester, polyoxyethylene glycerol difatty acid ester, polyglycerin fatty acid ester, polypropylene glycol monoester, aryl alkyl polyether alcohol, polyoxyethylene-polyoxypropylene copolymer (poloxamer), polyvinyl alcohol (PVA) and derivatives thereof, polyvinylpyrrolidone (PVP) and polysaccharides, preferably poloxamer, polyvinyl alcohol, polysorbates, polyvinyl pyrrolidone and polysaccharides, more preferably polyvinyl alcohol and polysaccharides.

The polysaccharides include, but are not limited to, starch and starch derivatives, methyl cellulose, ethyl cellulose, hydroxy cellulose, hydroxypropyl cellulose, hydroxypropyl methyl cellulose, gum arabic, chitosan derivatives, gellan gum, alginic acid derivatives, glucan derivatives and amorphous cellulose, preferably hydroxypropyl methyl cellulose, chitosan and derivatives thereof, amylopectin or glucan and derivatives thereof.

The surface active biomolecules include, but are not limited to, polyamino acids (such as polyaspartic acid or polyglutamic acid or analogs thereof), peptides (such as basic peptides), proteins (such as gelatin, casein, albumin, hirudin, starch hydroxyethylase, etc., preferably albumin).

The mass percentage of the surfactant (or stabilizer) in the external aqueous phase is generally 0.1-20%, preferably 0.5-15%, more preferably 1-10%.

Further, the surfactant-containing aqueous solution may further contain an inorganic salt to reduce the infiltration of the water-soluble active substance into the external aqueous phase during the solidification of the microparticles, and the mechanism is to increase the osmotic pressure of the external phase or reduce the solubility of the active substance in the external phase. For the active substances such as peptides, proteins, nucleic acids, antibodies, antigens, antibiotics, etc., zinc-ion-containing compounds are an ideal option, including but not limited to zinc acetate, zinc chloride, zinc sulfate, zinc hydrogen sulfate, zinc nitrate, zinc gluconate, zinc carbonate or any mixture thereof, and the weight percentage thereof in the aqueous solution is 0-5%, preferably 0.05-4%, more preferably 0.05-3%.

The salinity of the external aqueous phase can also be used to reduce the miscibility of the two phases, mainly to reduce the solubility of the organic solvent of the internal oil phase in the external aqueous phase. Suitable salts include, but are not limited to, water-soluble potassium salts or sodium salts of phosphoric acid, sulfuric acid, acetic acid and carbonic acid, Tris, MES and HEPES. In embodiments using a salt, the concentration of the salt is 0.01-10 M, more preferably 0.01-5 M, more preferably 0.05-2 M. The pH is 3-9, preferably 4-8, more preferably 5.5-7.5.

The amount of the external aqueous phase used is generally about 50 times by volume or more, preferably about 70 times by volume or more, and particularly preferably about 100 times by volume or more of the internal oil phase.

The method of forming a uniform emulsion is the same as the well-known emulsification method, using a device that generates a high shear force (such as a magnetic stirrer, a mechanical stirrer, a high speed homogenizer, an ultrasonic apparatus, a membrane emulsifier, a rotor-stator mixer, a static mixer, a high-pressure homogenizer, etc.) to mix the internal oil phase with the external aqueous phase to form a uniform emulsion.

The solvent removal in step 4) may use the following method:
(A) the organic solvent is removed by heating or depressurization (or combined heating);
(B) a gas stream blows the surface of the liquid, and the contact area between the liquid phase and the gas phase and the rate of emulsion stirring and circulation are controlled (such as JP-A-9-221418) to accelerate the volatilization of the organic solvent, the gas stream being preferably dried nitrogen; and
(C) the organic solvent is quickly removed by a hollow fiber film (for example, WO0183594), the hollow fiber film being preferably a silicone rubber pervaporation film, particularly a pervaporation film prepared from polydimethylsiloxane.

In step 4), the microparticles are collected by centrifugation, sieving or filtration.

The temperature of the ultrapure water used for washing the microparticles in step 4) is low temperature, which is maintained to be 12° C. or below, preferably 9° C. or below, more preferably 6° C. or below.

The ultrapure water used for washing in step 4) may further contain the inorganic salt (such as a zinc salt) in the external aqueous phase to reduce the infiltration of the water-soluble active substance into the aqueous phase during washing, thereby improving the drug encapsulation rate. The mass concentration of the inorganic salt in the ultrapure water is 0-3%, preferably 0.01-1.5%, more preferably 0.01-1%.

Further, the method further comprises the step of adding an additive which is added during the process of preparing the solid dispersion in step 1) or during the process of preparing the solid dispersion emulsion in step 2), preferably during the process of preparing the solid dispersion in step 1). The additive is dissolved or suspended in the internal oil phase. The additive may be added in the form of very fine powder having a particle size of less than 0.5 μm, preferably less than 0.1 μm, more preferably less than 0.05 μm.

The additive may impart additional characteristics to the active drug or microparticles, for example, increasing the stability of the microparticles, active drug or polymer, promoting controlled release of the active drug from the microparticles, or regulating the biological tissue permeability of the active drug. The additive is 0.01-10%, preferably 0.1-8%, more preferably 0.5-8%, of the sum of the mass of the water-soluble drug and the poorly water-soluble polymer.

The additive of the present invention includes, but is not limited to, at least one of saccharides, amino acids, fatty acids, alcohols, antioxidants and buffering agents.

The buffering agents include, but are not limited to, salts of inorganic acids or organic acids, such as salts of carbonic acid, acetic acid, oxalic acid, citric acid, phosphoric acid and hydrochloric acid, specifically, including, but not limited to, calcium carbonate, calcium hydroxide, calcium myristate, calcium oleate, calcium palmitate, calcium stearate, calcium phosphate, calcium acetate, magnesium acetate, magnesium carbonate, magnesium hydroxide, magnesium phosphate, magnesium myristate, magnesium oleate, magnesium palmitate, magnesium stearate, zinc carbonate, zinc hydroxide, zinc oxide, zinc myristate, zinc oleate, zinc acetate, zinc chloride, zinc sulfate, zinc hydrogen sulfate, zinc nitrate, zinc gluconate, zinc palmitate, zinc stearate, zinc phosphate, sodium carbonate, sodium hydrogen carbonate, sodium hydrogen sulfite, sodium thiosulfate, acetic acid-sodium acetate buffer salt, and any combination thereof, preferably zinc salts of inorganic acids or organic acids, more preferably zinc chloride. The buffering agent is 0-5%, preferably 0.01-3%, more preferably 0.01-2%, of the sum of the mass of the water-soluble drug and the poorly water-soluble polymer.

The antioxidants include, but are not limited to, tert-butyl p-hydroxyanisole, dibutyl phenol, tocopherol, isopropyl myristate, d-α-tocopheryl acetate, ascorbic acid, ascorbyl palmitate, butylated hydroxyanisol, butylated hydroxyquinone, hydroxycoumarin, butylated hydroxytoluene, gallo fatty acid ester (such as ethyl ester, propyl ester, octyl ester, lauryl ester), propyl hydroxybenzoate, trihydroxybutyrophenone, vitamin E, vitamin E-TPGS, ρ-hydroxybenzoate (such as methyl ester, ethyl ester, propyl ester, butyl ester), or any combination thereof. The antioxidant can effectively remove free radicals or peroxides in the sustained-release microparticles. The antioxidant is 0-1%, preferably 0-0.5%, more preferably 0-0.1%, of the sum of the mass of the water-soluble drug and the poorly water-soluble polymer.

The saccharides include, but are not limited to, monosaccharides, oligosaccharides and polysaccharides, and derivatives thereof, specifically, including but not limited to trehalose, glucose, sucrose, glycerin, erythritol, arabitol, xylitol, sorbitol, mannitol, glucuronic acid, iduronic acid, neuraminic acid, galacturonic acid, glucuronic acid, mannuronic acid, hyaluronic acid and salts thereof, chondroitin sulfate and salts thereof, heparin, inulin, chitin and derivatives thereof, dextrin, glucan and alginic acid and salts thereof, or any combination thereof, preferably sucrose, mannitol, xylitol, or any combination thereof. The saccharide is 0.1-10%, preferably 0.5-8%, more preferably 1-6% of the sum of the mass of the water-soluble drug and the poorly water-soluble polymer.

The amino acids include, but are not limited to, glycine, alanine, serine, aspartic acid, glutamic acid, threonine, tryptophan, lysine, hydroxylysine, histidine, arginine, cystine, cysteine, methionine, phenylalanine, leucine, isoleucine and derivatives thereof, preferably basic amino acids such as arginine, histidine, lysine, or any combination thereof. The amino acid is 0-4%, preferably 0-2%, more preferably 0.01-1%, of the sum of the mass of the water-soluble drug and the poorly water-soluble polymer.

The fatty acids include C12-C24 alkanoic acids and derivatives thereof, including, but not limited to, oleic acid, stearic acid, lauric acid, myristic acid, palmitic acid, arachidic acid, behenic acid and lignoceric acid, preferably stearic acid, behenic acid, palmitic acid, or any combination thereof. The fatty acid is 0-5%, preferably 0.01-4%, more preferably 0.05-3%, of the sum of the mass of the water-soluble drug and the poorly water-soluble polymer.

The alcohols include, but are not limited to, polyethylene glycol. The polyethylene glycol has a molecular weight of 400-6000 Da, preferably 400-4000 Da, more preferably 400-2000 Da. The alcohol is 0-5%, preferably 0.01-4%, more preferably 0.05-3%, of the sum of the mass of the water-soluble drug and the poorly water-soluble polymer.

The preparation for injection is required to be sterile, and the specific sterilization method is within the ordinary knowledge and skill of those skilled in the art, such as aseptic technique, hot pressing, ethylene oxide or gamma radiation to ensure sterility of the preparation. The preparation of the sustained-release microparticles of the present invention is preferably aseptic technique, such as filtering the external aqueous solution with a cellulose acetate membrane, filtering the PLGA/acetic acid solution with a polyethersulfone membrane, filtering the dichloromethane with a polytetrafluoroethylene membrane, and all the equipment is easily sealed and is equipped with an organic solvent recovery unit to prevent bacterial contamination and the diffusion of organic solvents into the air.

When the microparticles are used for injection administration, if the particle size is too large, it may easily cause needle blockage, a larger syringe needle must be used, and patients have more pain; and if the particle size is too small, the copolymer can not wrap the drug well, and a good sustained-release effect can not be achieved. Therefore, the present invention provides sustained-release microparticles obtained by the above-mentioned preparation method of sustained-release microparticles. The sustained-release microparticles prepared by the present invention preferably have a particle size of less than 200 μm. The sustained-release microparticles have a particle size of 10-200 μm, preferably 10-150 μm, more preferably 20-150 μm. The particle size of the sustained-release microparticles is measured by a dynamic light scattering method (for example, laser diffraction method) or a microscopic technique (for example, scanning electron microscopy).

The sustained-release microparticles of the present invention can encapsulate a large amount of active substances, and the dosage may be appropriately selected according to the type and content of the active substance, the dosage form, the duration of release, the subject to be administered, the route of administration, the purpose of administration, the target disease and symptoms, and the like. However, the dosage can be considered satisfactory as long as the active substance can be maintained in the effective concentration of the drug for the desired duration in vivo.

In the sustained-release microparticles of the present invention, the mass percentage of the active agent is about 1-40%, preferably 3-35%, more preferably 5-30%.

When a range is stated herein, it is meant to include any range or combination of ranges.

When the sustained-release microparticles are administered in the form of a suspension, they can be prepared into a suspension preparation with a suitable dispersion medium.

The dispersion medium includes at least one of nonionic surfactants, polyoxyethylene castor oil derivatives, cellulose thickeners, sodium alginate, hyaluronic acid, dextrin and starch. Alternatively, it may be combined with other components such as isotonic agents (for example, sodium chloride, mannitol, glycerol, sorbitol, lactose, xylitol, maltose, galactose, sucrose, glucose, etc.), pH adjusters (for example, carbonic acid, acetic acid, oxalic acid, citric acid, phosphoric acid, hydrochloric acid or salts thereof, such as sodium carbonate, sodium bicarbonate, etc.), preservatives (for example, p-hydroxybenzoates, propyl p-hydroxybenzoate, benzyl alcohol, chlorobutanol, sorbic acid, boric acid, etc.) to form an aqueous solution, or it is subsequently solidified by freeze drying, reduced pressure drying, spray drying, etc., and the solidified product is dissolved in water for injection to obtain the dispersion medium dispersed with sustained-release microparticles.

Further, the sustained-release injection can also be obtained by the following method: dispersing the sustained-release microparticles in vegetable oil (such as sesame oil and corn oil) or in vegetable oil to which a phospholipid such as lecithin is added, or in a medium chain triglyceride to obtain an oily suspension.

The water-soluble drug sustained-release composition prepared by the present invention, in particular, the sustained-release composition of the protein, nucleic acid and peptide drug may also be a rod and a sheet, and the preparation method mainly comprises the following two steps:
I. preparing a solid dispersion of a water-soluble drug and a biodegradable and biocompatible polymer; and
II. after heating the solid dispersion mentioned above, molding by a method well known to those skilled in the art such as compression molding, extrusion molding or the like, and cooling to obtain a rod-shaped or sheet-shaped sustained-release composition.

Further, the sustained-release composition of the water-soluble drug, especially a protein, nucleic acid and peptide drug of the present invention is a rod-shaped or sheet-shaped implant, and the preparation method is mainly as follows: preparing sustained-release microparticles according to the above-mentioned method for preparing sustained-release microparticles, and preparing the microparticles into the rod or sheet by a molding method well known to those skilled in the art.

The sustained-release microparticles obtained by the present invention can be used in the form of granules, suspensions, implants, injections, adhesive preparations, and the like, and can be administered orally or parenterally (intramuscular injection, subcutaneous injection, transdermal administration, mucosal administration (buccal, intravaginal, rectal, etc.)).

The implant of the present invention is based on a biodegradable material and has a thin rod shape, a round rod shape or a sheet shape (disc shape), and can be implanted into the body by injection or surgery, and does not require surgical removal after the drug is completely released. The implant can easily obtain a high encapsulation rate and drug loading rate, has a low burst release rate, and can continuously release the active drug of the therapeutic dose for a period of one month to several months, thereby greatly reducing the medical cost and improving patient compliance.

The present invention has the following beneficial effects: in the present invention, the whole preparation process of the sustained-release microparticles is at normal or low temperature, which is highly advantageous for the preparation of a polymer-based composition from a high-temperature-sensitive drug, particularly a protein, nucleic acid and peptide drug, and the bioactivity of the active substance can be maintained to the greatest extent throughout the process compared to the disclosed technology; at the same time, the prepared sustained-release microparticles have an excellent sustained-release effect close to zero order, and the drug concentration is stabilized during the release, which overcomes the defects that the microparticles obtained by the conventional S/O/W process of pre-preparing the drug microparticles have no drug release in the earlier stage and a rapid release of the drug in the later stage; and in addition, the sustained-release microparticles have a higher drug loading rate and drug encapsulation rate.

After the administration of the sustained-release microparticles of the present invention, active substances such as proteins, peptides, nucleic acids, alkaloids and the like can be continuously delivered in the body for a period of time, and the release period is as long as several weeks or several months.

DETAILED DESCRIPTION OF THE INVENTION

Figure 1:
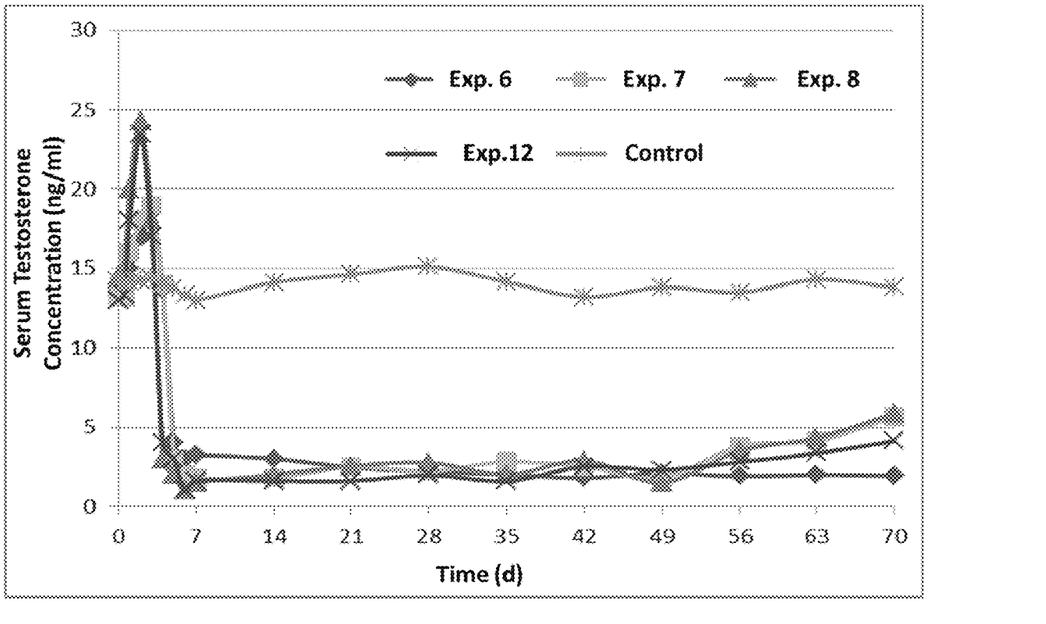
FIG. is a serum testosterone concentration-time curve graph of rats administered with goserelin microparticles of Embodiment 6, leuprorelin microparticles of Embodiment 7, triptorelin microparticles of Embodiment 8 and buserelin microparticles of Embodiment 12 according to the present invention.

The present invention will be further described with reference to specific embodiments in order to better illustrate the objectives, technical solutions and advantages of the present invention.

Embodiment 1: Preparation of Glucagon/PLA Microparticles (I) Preparation of Solid Dispersion 0.99 g of PLA (molecular weight of 25 kDa, terminal ester group) was dissolved in about 5.50 mL of glacial acetic acid, then 0.01 g of sermorelin acetate, 0.05 g of xylitol and 0.05 g of zinc hydroxide were added and dissolved under vortex, the mixture was slowly poured into anhydrous diethyl ether (8° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 5.50 g of dichloromethane to obtain an internal oil phase, then the internal oil phase was poured into 210 mL of 0.1% (w/w) polyvinyl alcohol aqueous solution which had been previously thermostated to about 6° C., and an S/O/W emulsion was prepared by emulsification by using a wheeled homomixer (running speed of about 7000 rpm, 5 min). The S/O/W emulsion was transferred to a sealed glass flask and mechanically stirred for about 3 hours (500 rpm) to solidify the microparticles, and then the microparticles were collected by centrifugation (about 2500 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of glucagon in the obtained microparticles was 0.92%, and the particle size of the microparticles was 45-110 μm.

Embodiment 2: Preparation of Ziconotide/PLGA Microparticles (I) Preparation of Solid Dispersion 0.97 g of PLGA (molecular weight of 25 kDa, monomer ratio 90/10, terminal ester group) was dissolved in about 5.39 mL of glacial acetic acid, then 0.03 g of ziconotide acetate, 0.05 g of xylitol and 0.03 g of zinc chloride were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 5.39 g of dichloromethane to obtain an internal oil phase, then the internal oil phase was poured into 290 mL of 0.5% (w/w) polyvinyl alcohol aqueous solution which had been previously thermostated to about 4° C., and an S/O/W emulsion was prepared by using a high-speed homogenizer (rotor speed of about 5000 rpm, 5 min). The S/O/W emulsion was mechanically stirred for about 3.5 hours (500 rpm) to solidify the microparticles, and then the microparticles were collected by centrifugation (about 3500 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of ziconotide in the obtained microparticles was 2.73%, and the particle size of the microparticles was 20-80 μm.

Embodiment 3: Preparation of Cosyntropin/PLGA Microparticles (I) Preparation of Solid Dispersion 0.95 g of PLGA (molecular weight of 30 kDa, monomer ratio of 85/15, terminal ester group) was dissolved in about 6.33 mL of glacial acetic acid/acetonitrile mixed solution, then 0.05 g of cosyntropin acetate was added and dissolved under vortex, the mixture was slowly poured into cyclohexane (6° C.) under stirring to obtain a white precipitate, the white precipitate was collected and extracted with cyclohexane for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 6.33 g of chloroform to obtain an internal oil phase, then the internal oil phase was poured into 480 mL of 1% (w/w) hydroxypropyl methylcellulose aqueous solution which had been previously thermostated to about 4° C., and an S/O/W emulsion (membrane pore size of 20-50 μm, 3 cycles) was prepared by using an SPG membrane emulsifier. The S/O/W emulsion was mechanically stirred for about 3.5 hours (500 rpm) to solidify the microparticles, and then the microparticles were collected by centrifugation (about 3500 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of cosyntropin in the obtained microparticles was 4.63%, and the particle size of the microparticles was 45-85 μm.

Embodiment 4: Preparation of Somatostatin/PLGA Microparticles (I) Preparation of Solid Dispersion 0.90 g of PLGA (molecular weight of 35 kDa, monomer ratio of 75/25, terminal ester group) was dissolved in about 7.50 mL of trifluoroacetic acid, then 0.1 g of somatostatin was added and dissolved under vortex, the mixture was slowly poured into n-hexane (6° C.) under stirring to obtain a white precipitate, the white precipitate was collected and extracted with n-hexane for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 7.50 g of dichloromethane to obtain an internal oil phase, then the internal oil phase was poured into 450 mL of 2% (w/w) albumin aqueous solution which had been previously thermostated to about 4° C., and an S/O/W emulsion was prepared by using a static mixer (rotation speed of about 5000 rpm, 3 cycles). The S/O/W emulsion was transferred to a sealed glass flask and mechanically stirred for about 3.5 hours (500 rpm) to solidify the microparticles, and then the microparticles were collected by centrifugation (about 3500 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of somatostatin in the obtained microparticles was 9.00%, and the particle size of the microparticles was 48-99 μm.

Embodiment 5: Preparation of Terlipressin/PLGA Microparticles (I) Preparation of Solid Dispersion 0.85 g of PLGA (molecular weight of 40 kDa, monomer ratio of 65/35, terminal ester group) was dissolved in about 8.50 mL of dimethyl sulfoxide, then 0.15 g of terlipressin acetate was added and dissolved under vortex, the mixture was slowly poured into n-heptane (6° C.) under stirring to obtain a white precipitate, the white precipitate was collected and extracted with n-heptane for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 8.50 g of benzyl alcohol to obtain an internal oil phase, then the internal oil phase was poured into 580 mL of 3% (w/w) poloxamer aqueous solution which had been previously thermostated to about 4° C., and an S/O/W emulsion was prepared by mechanical stirring (1000 rpm, 3 min). The S/O/W emulsion was mechanically stirred for about 3.5 hours (500 rpm) to solidify the microparticles, and then the microparticles were collected by centrifugation (about 3000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of terlipressin in the obtained microparticles was 13.92%, and the particle size of the microparticles was 25-100 μm.

Embodiment 6: Preparation of Goserelin/PLGA Microparticles (I) Preparation of Solid Dispersion 0.9625 g of PLGA (molecular weight of 35 kDa, monomer ratio of 75/25, terminal carboxyl group) was dissolved in about 6.42 mL of glacial acetic acid, then 0.0375 g of goserelin acetate and 0.08 g of xylitol were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 6.42 g of dichloromethane to obtain an internal oil phase, then the internal oil phase was poured into 440 mL of 2% (w/w) polyvinyl alcohol aqueous solution which had been previously thermostated to about 4° C., and an S/O/W emulsion was prepared by mechanical stirring (900 rpm, 5 min). The S/O/W emulsion was mechanically stirred for about 3.5 hours (400 rpm) to solidify the microparticles, and then the microparticles were collected by centrifugation (about 3000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of goserelin in the obtained microparticles was 3.42%, and the particle size of the microparticles was 20-77 μm.

Embodiment 7: Preparation of Leuprorelin/PLGA Microparticles (I) Preparation of Solid Dispersion 0.925 g of PLGA (molecular weight of 40 kDa, monomer ratio of 65/35, terminal carboxyl group) was dissolved in about 7.71 mL of glacial acetic acid, then 0.075 g of leuprorelin acetate and 0.06 g of xylitol were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 7.71 g of dichloromethane to obtain an internal oil phase, then the internal oil phase was poured into 410 mL of 3% (w/w) polyvinyl alcohol aqueous solution which had been previously thermostated to about 4° C., and an S/O/W emulsion was prepared by mechanical stirring (800 rpm, 5 min). The S/O/W emulsion was mechanically stirred for about 4 hours (350 rpm) to solidify the microparticles, and then the microparticles were collected by centrifugation (about 3000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of leuprorelin in the obtained microparticles was 7.04%, and the particle size of the microparticles was 28-85 μm.

Embodiment 8: Preparation of Triptorelin/PLGA Microparticles (I) Preparation of Solid Dispersion 0.85 g of PLGA (molecular weight of 45 kDa, monomer ratio of 50/50, terminal carboxyl group) was dissolved in about 8.50 mL of glacial acetic acid, then 0.15 g of triptorelin acetate and 0.03 g of xylitol were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 8.50 g of dichloromethane to obtain an internal oil phase, then the internal oil phase was poured into 650 mL of 4% (w/w) polyvinyl alcohol aqueous solution which had been previously thermostated to about 4° C., and an S/O/W emulsion was prepared by mechanical stirring (1000 rpm, 5 min). The S/O/W emulsion was mechanically stirred for about 4 hours (500 rpm) to solidify the microparticles, and then the microparticles were collected by centrifugation (about 3000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of triptorelin in the obtained microparticles was 13.91%, and the particle size of the microparticles was 30-92 μm.

Embodiment 9: Preparation of Leuprorelin/PLGA Microparticles (I) Preparation of Solid Dispersion 0.80 g of PLGA (molecular weight of 50 kDa, monomer ratio of 50/50, terminal carboxyl group) was dissolved in about 10.00 mL of glacial acetic acid, then 0.20 g of leuprorelin acetate was added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 10.00 g of dichloromethane to obtain an internal oil phase, then the internal oil phase was poured into 910 mL of 6% (w/w) polyvinyl alcohol aqueous solution which had been previously thermostated to about 4° C., and an S/O/W emulsion was prepared by mechanical stirring (1400 rpm, 5 min). The S/O/W emulsion was mechanically stirred for about 4 hours (600 rpm) to solidify the microparticles, and then the microparticles were collected by centrifugation (about 4000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of leuprorelin in the obtained microparticles was 18.43%, and the particle size of the microparticles was 20-82 μm.

Embodiment 10: Preparation of Antide/PLGA Microparticles (I) Preparation of Solid Dispersion 0.82 g of PLGA (molecular weight of 55 kDa, monomer ratio of 50/50, terminal carboxyl group) was dissolved in about 11.71 mL of glacial acetic acid, then 0.18 g of antide acetate and 0.02 g of xylitol were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 11.71 g of dichloromethane to obtain an internal oil phase, then the internal oil phase was poured into 700 mL of 4% (w/w) polyvinyl alcohol aqueous solution which had been previously thermostated to about 4° C., and an S/O/W emulsion was prepared by mechanical stirring (900 rpm, 5 min). The S/O/W emulsion was mechanically stirred for about 4 hours (400 rpm) to solidify the microparticles, and then the microparticles were collected by centrifugation (about 4000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of antide in the obtained microparticles was 17.11%, and the particle size of the microparticles was 25-110 μm.

Embodiment 11: Preparation of Nafarelin/PLGA Microparticles (I) Preparation of Solid Dispersion 0.80 g of PLGA (molecular weight of 65 kDa, monomer ratio of 65/35, terminal carboxyl group) was dissolved in about 13.33 mL of glacial acetic acid, then 0.20 g of nafarelin acetate, 0.05 g of sucrose and 0.01 g of stearic acid were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 13.33 g of dichloromethane to obtain an internal oil phase, then the internal oil phase was poured into 910 mL of 5% (w/w) polyvinyl alcohol aqueous solution which had been previously thermostated to about 4° C., and an S/O/W emulsion was prepared by mechanical stirring (1300 rpm, 5 min). The S/O/W emulsion was mechanically stirred for about 4 hours (400 rpm) to solidify the microparticles, and then the microparticles were collected by centrifugation (about 3500 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of nafarelin in the obtained microparticles was 18.13%, and the particle size of the microparticles was 30-115 μm.

Embodiment 12: Preparation of Buserelin/PLGA Microparticles (I) Preparation of Solid Dispersion 0.75 g of PLGA (molecular weight of 75 kDa, monomer ratio of 50/50, terminal carboxyl group) was dissolved in about 15.00 mL of glacial acetic acid, then 0.25 g of buserelin acetate and 0.04 g of mannitol were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 15.00 g of dichloromethane to obtain an internal oil phase, then the internal oil phase was poured into 1.1 L of 6% (w/w) polyvinyl alcohol aqueous solution which had been previously thermostated to about 4° C., and an S/O/W emulsion was prepared by mechanical stirring (1200 rpm, 5 min). The S/O/W emulsion was mechanically stirred for about 4 hours (500 rpm) to solidify the microparticles, and then the microparticles were collected by centrifugation (about 3000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of buserelin in the obtained microparticles was 23.30%, and the particle size of the microparticles was 30-125 μm.

Embodiment 13: Preparation of Alarelin/PLGA Microparticles (I) Preparation of Solid Dispersion 0.70 g of PLGA (molecular weight of 90 kDa, monomer ratio of 65/35, terminal carboxyl group) was dissolved in about 17.50 mL of glacial acetic acid, then 0.30 g of alarelin acetate, 0.05 g of mannitol and 0.03 g of PEG-400 were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 17.50 g of dichloromethane to obtain an internal oil phase, then the internal oil phase was poured into 1.3 L of 8% (w/w) polyvinyl alcohol aqueous solution which had been previously thermostated to about 4° C., and an S/O/W emulsion was prepared by mechanical stirring (1500 rpm, 5 min). The S/O/W emulsion was mechanically stirred for about 4 hours (500 rpm) to solidify the microparticles, and then the microparticles were collected by centrifugation (about 3000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of alarelin in the obtained microparticles was 26.57%, and the particle size of the microparticles was 24-130 μm.

Embodiment 14: Preparation of Octreotide/PLGA Microparticles (I) Preparation of Solid Dispersion 0.65 g of PLGA (molecular weight of 110 kDa, monomer ratio of 50/50, terminal carboxyl group) was dissolved in about 21.67 mL of glacial acetic acid, then 0.35 g of octreotide acetate and 0.01 g of xylitol were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 21.67 g of dichloromethane to obtain an internal oil phase, then the internal oil phase was poured into 1.6 L of 10% (w/w) polyvinyl alcohol aqueous solution which had been previously thermostated to about 4° C., and an S/O/W emulsion was prepared by mechanical stirring (1500 rpm, 5 min). The S/O/W emulsion was mechanically stirred for about 5 hours (500 rpm) to solidify the microparticles, and then the microparticles were collected by centrifugation (about 3000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of octreotide in the obtained microparticles was 32.8%, and the particle size of the microparticles was 20-100 μm.

Embodiment 15: Preparation of Bremelanotide/PLGA Microparticles (I) Preparation of Solid Dispersion 0.60 g of PLGA (molecular weight of 130 kDa, monomer ratio of 50/50, terminal carboxyl group) was dissolved in about 30.00 mL of glacial acetic acid, then 0.40 g of bremelanotide acetate and 0.005 g of xylitol were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 30.00 g of dichloromethane to obtain an internal oil phase, then the internal oil phase was poured into 2 L of 15% (w/w) polyvinyl alcohol aqueous solution which had been previously thermostated to about 4° C., and an S/O/W emulsion was prepared by mechanical stirring (1800 rpm, 5 min). The S/O/W emulsion was mechanically stirred for about 5 hours (700 rpm) to solidify the microparticles, and then the microparticles were collected by centrifugation (about 3000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of bremelanotide in the obtained microparticles was 35.12%, and the particle size of the microparticles was 15-83 μm.

Embodiment 16: Preparation of Hexarelin/PLGA Microparticles (I) Preparation of Solid Dispersion 0.50 g of PLGA (molecular weight of 150 kDa, monomer ratio of 50/50, terminal carboxyl group) was dissolved in about 50.00 mL of glacial acetic acid, then 0.50 g of hexarelin acetate and 0.001 g of xylitol were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step 1 was uniformly dispersed in about 50.00 g of dichloromethane to obtain an internal oil phase, then the internal oil phase was poured into 2.6 L of 20% (w/w) polyvinyl alcohol aqueous solution which had been previously thermostated to about 4° C., and an S/O/W emulsion was prepared by emulsification by using a wheeled homomixer (running speed of about 7000 rpm, 5 min). The S/O/W emulsion was transferred into a sealed glass flask and mechanically stirred for about 5 hours (800 rpm) to solidify the microparticles, and then the microparticles were collected by centrifugation (about 4000 rpm, 5 min) using a centrifuge. The microparticles were again dispersed in ultrapure water (5° C.) for washing for 2 min, then the washed microparticles were collected by centrifugation, and the washing step was repeated for about 5 times, followed by freeze drying in a freeze dryer to obtain the microparticles. The content of hexarelin in the obtained microparticles was 42.38%, and the particle size of the microparticles was 22-87 μm.

Embodiment 17: Preparation of Exendin-4 Derivative/PLGA Microparticles (I) Preparation of Solid Dispersion The solid dispersion contains the following components in percentage by mass: water-soluble drug: exendin-4 derivatives 20%, poorly water-soluble polymer: PLGA 79.5%, and additive: xylitol 0.5%, wherein the molecular weight of the PLGA is 50 kDa, wherein the ratio of lactide to glycolide is 50/50, and the PLGA has a terminal carboxyl group.

(1) Preparation of exendin-4 derivatives: 10 kDa PEG-NHS ester was prepared, then reacted with asparagine at position 28 in exendin-4 in a PBS buffer, and the product was separated and purified by ion exchange and gel chromatography, and concentrated and freeze-dried to obtain the exendin-4 derivatives.

(2) The poorly water-soluble polymer was completely dissolved in glacial acetic acid, and then a water-soluble drug and an additive were added and completely dissolved, the poorly water-soluble polymer being 6.5% by mass of glacial acetic acid; and the mixture was poured into anhydrous diethyl ether (6° C.) to obtain a white precipitate, the precipitate was collected and extracted with anhydrous diethyl ether for 5 times, and the precipitate was collected and dried in a vacuum drying oven for 24 h (10° C.) to obtain a solid dispersion.

(II) Preparation of Microparticles

The solid dispersion obtained in step I was uniformly dispersed in about 12 times of dichloromethane to obtain an internal oil phase, then the internal oil phase was poured into 1 L of 4% (w/w) polyvinyl alcohol aqueous solution which had been previously thermostated to about 5° C., and an S/O/W emulsion was prepared by mechanical stirring (1200 rpm, 5 min). The S/O/W emulsion was mechanically stirred for about 4 hours (600 rpm) to solidify the microparticles, and then the microparticles were collected by centrifugation (about 3500 rpm, 5 min) using a centrifuge. The microparticles were washed with n-heptane for about 5 times, the microparticles washed with n-heptane were dispersed again in ultrapure water (5° C.) for washing for about 2 times, and the microparticles washed with ultrapure water were collected by centrifugation, and freeze-dried in a freeze dryer to obtain the microparticles. The content of exendin-4 derivatives in the obtained microparticles was 18.11%, and the particle size of the microparticles was 29-116 μm.

Embodiment 18: Preparation of Exendin-4 Derivative/PLGA Microparticles (I) Preparation of Solid Dispersion The solid dispersion contains the following components in percentage by mass: water-soluble drug: exendin-4 derivatives 15%, poorly water-soluble polymer: PLGA 84%, and additive: xylitol 1%, wherein the molecular weight of the PLGA is 50 kDa, wherein the ratio of lactide to glycolide is 50/50, and the PLGA has a terminal carboxyl group.

(1) Preparation of exendin-4 derivatives: an exendin-4 variant in which asparagine at position 28 in exendin-4 was replaced with cysteine was prepared by a solid phase polypeptide synthesis method, and then reacted with 10 kDa Y-type monomethoxypolyethylene glycol-maleimide in a PBS buffer, and the product was separated and purified by ion exchange and gel chromatography, and concentrated and freeze-dried to obtain exendin-4 derivatives.

(2) The poorly water-soluble polymer was completely dissolved in glacial acetic acid, and then a water-soluble drug and an additive were added and completely dissolved, the poorly water-soluble polymer being 6.5% by mass of glacial acetic acid; and the mixture was poured into anhydrous diethyl ether (6° C.) to obtain a white precipitate, the precipitate was collected and extracted with anhydrous diethyl ether for 5 times, and the precipitate was collected and dried in a vacuum drying oven for 24 h (10° C.) to obtain a solid dispersion.

(II) Preparation of Microparticles

The solid dispersion obtained in step I was uniformly dispersed in about 13 times of dichloromethane to obtain an internal oil phase, then the internal oil phase was poured into 970 mL of 4% (w/w) polyvinyl alcohol aqueous solution which had been previously thermostated to about 5° C., and an S/O/W emulsion was prepared by mechanical stirring (1200 rpm, 5 min). The S/O/W emulsion was mechanically stirred for about 4 hours (500 rpm) to solidify the microparticles, and then the microparticles were collected by centrifugation (about 3500 rpm, 5 min) using a centrifuge. The microparticles were washed with n-heptane for about 5 times, the microparticles washed with n-heptane were dispersed again in ultrapure water (5° C.) for washing for about 2 times, and the microparticles washed with ultrapure water were collected by centrifugation, and freeze-dried in a freeze dryer to obtain the microparticles. The content of exendin-4 derivatives in the obtained microparticles was 13.08%, and the particle size of the microparticles was 30-122 μm.

Embodiment 19: Preparation of Exendin-4 Derivative/PLGA Microparticles (I) Preparation of Solid Dispersion The solid dispersion contains the following components in percentage by mass: water-soluble drug: exendin-4 derivatives 20%, poorly water-soluble polymer: PLGA 78%, and additive: sorbitol 2%, wherein the molecular weight of the PLGA is 55 kDa, wherein the ratio of lactide to glycolide is 50/50, and the PLGA has a terminal carboxyl group.

(1) Preparation of exendin-4 derivatives: an exendin-4 variant in which arginine at position 20 in exendin-4 was replaced with cysteine was prepared by a solid phase polypeptide synthesis method, and then reacted with 5 kDa monomethoxypolyethylene glycol-maleimide in a PBS buffer, and the product was separated and purified by ion exchange and gel chromatography, and concentrated and freeze-dried to obtain exendin-4 derivatives.

(2) The poorly water-soluble polymer was completely dissolved in glacial acetic acid, and then a water-soluble drug and an additive were added and completely dissolved, the poorly water-soluble polymer being 6% by mass of glacial acetic acid; and the mixture was poured into anhydrous diethyl ether (6° C.) to obtain a white precipitate, the precipitate was collected and extracted with anhydrous diethyl ether for 5 times, and the precipitate was collected and dried in a vacuum drying oven for 24 h (10° C.) to obtain a solid dispersion.

(II) Preparation of Microparticles

The solid dispersion obtained in step I was uniformly dispersed in about 14 times of dichloromethane to obtain an internal oil phase, then the internal oil phase was poured into 1 L of 4% (w/w) polyvinyl alcohol aqueous solution which had been previously thermostated to about 5° C., and an S/O/W emulsion was prepared by mechanical stirring (1400 rpm, 5 min). The S/O/W emulsion was mechanically stirred for about 4 hours (500 rpm) to solidify the microparticles, and then the microparticles were collected by centrifugation (about 3500 rpm, 5 min) using a centrifuge. The microparticles were washed with n-heptane for about 5 times, the microparticles washed with n-heptane were dispersed again in ultrapure water (5° C.) for washing for about 2 times, and the microparticles washed with ultrapure water were collected by centrifugation, and freeze-dried in a freeze dryer to obtain the microparticles. The content of exendin-4 derivatives in the obtained microparticles was 18.20%, and the particle size of the microparticles was 30-120 μm.

Embodiment 20: Preparation of Alarelin Derivative/PLGA Microparticles (I) Preparation of Solid Dispersion The solid dispersion contains the following components in percentage by mass: water-soluble drug: alarelin derivatives 16%, poorly water-soluble polymer: PLGA 81%, and additive: xylitol 3%, wherein the molecular weight of the PLGA is 45 kDa, wherein the ratio of lactide to glycolide is 50/50, and the PLGA has a terminal carboxyl group.

(1) Preparation of alarelin derivatives: an alarelin variant in which serine at position 4 in alarelin was replaced with cysteine was prepared by a solid phase polypeptide synthesis method, and then reacted with 20 kDa monomethoxypolyethylene glycol-maleimide in a PBS buffer, and the product was separated and purified by ion exchange and gel chromatography, and concentrated and freeze-dried to obtain alarelin derivatives.

(2) The poorly water-soluble polymer was completely dissolved in glacial acetic acid, and then a water-soluble drug and an additive were added and completely dissolved, the poorly water-soluble polymer being 7% by mass of glacial acetic acid; and the mixture was poured into anhydrous diethyl ether (6° C.) to obtain a white precipitate, the precipitate was collected and extracted with anhydrous diethyl ether for 5 times, and the precipitate was collected and dried in a vacuum drying oven for 24 h (10° C.) to obtain a solid dispersion.

(II) Preparation of Microparticles

The solid dispersion obtained in step I was uniformly dispersed in about 11 times of dichloromethane to obtain an internal oil phase, then the internal oil phase was poured into 970 mL of 2% (w/w) polyvinyl alcohol aqueous solution which had been previously thermostated to about 4° C., and an S/O/W emulsion was prepared by mechanical stirring (1200 rpm, 5 min). The S/O/W emulsion was mechanically stirred for about 4 hours (500 rpm) to solidify the microparticles, and then the microparticles were collected by centrifugation (about 3500 rpm, 5 min) using a centrifuge. The microparticles were washed with n-heptane for about 5 times, the microparticles washed with n-heptane were dispersed again in ultrapure water (5° C.) for washing for about 2 times, and the microparticles washed with ultrapure water were collected by centrifugation, and freeze-dried in a freeze dryer to obtain the microparticles. The content of alarelin derivatives in the obtained microparticles was 13.55%, and the particle size of the microparticles was 29-121 μm.

Embodiment 21: Preparation of Thymopentin Derivative/PLGA Microparticles

The solid dispersion contains the following components in percentage by mass: water-soluble drug: thymopentin derivatives 12%, poorly water-soluble polymer: PLGA 84%, and additive: xylitol 4%, wherein the molecular weight of the PLGA is 40 kDa, wherein the ratio of lactide to glycolide is 50/50, and the PLGA has a terminal carboxyl group.

(1) Preparation of thymopentin derivatives: 10 kDa PEG-NHS ester was prepared, then reacted with lysine at position 2 in thymopentin in a PBS buffer, and the product was separated and purified by ion exchange and gel chromatography, and concentrated and freeze-dried to obtain the thymopentin derivatives.

(2) The poorly water-soluble polymer was completely dissolved in glacial acetic acid, and then a water-soluble drug and an additive were added and completely dissolved, the poorly water-soluble polymer being 6.5% by mass of glacial acetic acid; and the mixture was poured into anhydrous diethyl ether (6° C.) to obtain a white precipitate, the precipitate was collected and extracted with anhydrous diethyl ether for 5 times, and the precipitate was collected and dried in a vacuum drying oven for 24 h (10° C.) to obtain a solid dispersion.

(II) Preparation of Microparticles

The solid dispersion obtained in step I was uniformly dispersed in about 10 times of dichloromethane to obtain an internal oil phase, then the internal oil phase was poured into 970 mL of 3% (w/w) polyvinyl alcohol aqueous solution which had been previously thermostated to about 4° C., and an S/O/W emulsion was prepared by mechanical stirring (1400 rpm, 5 min). The S/O/W emulsion was mechanically stirred for about 4 hours (500 rpm) to solidify the microparticles, and then the microparticles were collected by centrifugation (about 3500 rpm, 5 min) using a centrifuge. The microparticles were washed with n-heptane for about 5 times, the microparticles washed with n-heptane were dispersed again in ultrapure water (5° C.) for washing for about 2 times, and the microparticles washed with ultrapure water were collected by centrifugation, and freeze-dried in a freeze dryer to obtain the microparticles. The content of thymopentin derivatives in the obtained microparticles was 10.68%, and the particle size of the microparticles was 35-132 μm.

Embodiment 22: Preparation of Mipomersen/PLGA Microparticles (I) Preparation of Solid Dispersion 0.80 g of PLGA (molecular weight of 30 kDa, monomer ratio of 50/50, terminal carboxyl group) was dissolved in about 6.53 mL of glacial acetic acid/acetonitrile mixed solution, then 0.20 g of mipomersen sodium and 0.01 g of xylitol were added and dissolved under vortex, the mixture was slowly poured into anhydrous diethyl ether (6° C.) under stirring to obtain a white precipitate, the white precipitate was collected and extracted with n-hexane for about 5 times, and the precipitate was collected and dried in a vacuum drying oven for 24 h (10° C.) to obtain a solid dispersion.

(II) Preparation of Microparticles

The solid dispersion obtained in step I was uniformly dispersed in about 6.53 g of tetrachloroethylene to obtain an internal oil phase, then the internal oil phase was poured into 500 ml of 4% (w/w) polyvinyl alcohol aqueous solution which had been previously thermostated to about 6° C., and an S/O/W emulsion was prepared by mechanical stirring (1000 rpm, 5 min). The S/O/W emulsion was mechanically stirred for about 3.5 hours (500 rpm) to solidify the microparticles, and then the microparticles were collected by centrifugation (about 3500 rpm, 5 min) using a centrifuge. The microparticles were washed with cyclohexane for about 5 times, the microparticles washed with cyclohexane were dispersed again in ultrapure water (5° C.) for washing for about 2 times, and the microparticles washed with ultrapure water were collected by centrifugation, and freeze-dried in a freeze dryer to obtain the microparticles. The content of mipomersen in the obtained microparticles was 18.00%, and the particle size of the microparticles was 30-114 μm.

Embodiment 23: Preparation of Interleukin/PLGA Microparticles (I) Preparation of Solid Dispersion 0.82 g of PLGA (molecular weight of 35 kDa, monomer ratio of 50/50, terminal carboxyl group) was dissolved in about 6.12 mL of glacial acetic acid, then 0.18 g of interleukin and 0.02 g of xylitol were added and dissolved under vortex, the mixture was slowly poured into anhydrous diethyl ether (6° C.) under stirring to obtain a white precipitate, the white precipitate was collected and extracted with anhydrous diethyl ether for about 5 times, and the precipitate was collected and dried in a vacuum drying oven for 24 h (10° C.) to obtain a solid dispersion.

(II) Preparation of Microparticles

The solid dispersion obtained in step I was uniformly dispersed in about 6.12 g of dichloromethane/chloroform mixed solution to obtain an internal oil phase, then the internal oil phase was poured into 500 ml of 4% (w/w) polyvinyl alcohol aqueous solution which had been previously thermostated to about 5° C., and an S/O/W emulsion was prepared by mechanical stirring (1000 rpm, 5 min). The S/O/W emulsion was transferred to a sealed glass flask and mechanically stirred for about 4 hours (500 rpm) to solidify the microparticles, and then the microparticles were collected by centrifugation (about 3500 rpm, 5 min) using a centrifuge. The microparticles were washed with an n-heptane/n-hexane mixed solution for about 5 times, the microparticles washed with the n-heptane/n-hexane mixed solution were dispersed again in ultrapure water (5° C.) for washing for about 2 times, and the microparticles washed with ultrapure water were collected by centrifugation, and freeze-dried in a freeze dryer to obtain the microparticles. The content of interleukin in the obtained microparticles was 16.02%, and the particle size of the microparticles was 29-117 μm.

Embodiment 24: Preparation of Leuprorelin/PLGA Sustained-Release Implant

The dried solid dispersion prepared in step I of Embodiment 9 was added in a 1 mm*10 mm mold (the inner cavity was cylindrical, the diameter of the round bottom was 1 mm, and the depth was about 10 mm), and subjected to compression molding after the temperature was raised to about 45° C. to obtain a cylindrical (1 mm*5.27 mm) leuprorelin sustained-release implant. The content of leuprorelin in the obtained implant was 18.79%.

Embodiment 25: Preparation of Leuprorelin/PLGA Sustained-Release Implant

The microparticles obtained in step II of Embodiment 9 were fed into a hot melt extruder, and hot melt extruded into strips having a diameter of about 1 mm, and after cooling, the strips were cut into a cylindrical leuprorelin sustained-release implant having a length of about 5 mm. The content of leuprorelin in the obtained implant was 18.41%.

Embodiment 26

The method for analyzing the drug loading rate and drug encapsulation rate of the microparticles and implants in the above embodiments was as follows: taking 5 mg of microparticles or implant, dissolving in 50 mL of acetonitrile (ACN), then adding 500 μL of 0.1% TFA, thoroughly mixing, centrifugating to obtain the supernatant, and analyzing the concentration of the drug by high performance liquid chromatography. The ratio of the mass of the drug encapsulated in the microparticles (or implant) to the dose is the encapsulation rate of the drug, and the ratio of the mass of the drug encapsulated in the microparticles (or implant) to the mass of the microparticles (or implant) is the drug loading rate of the drug. All the experiments were repeated for 3 or more than 3 times.

Liquid chromatograph: Agilent 1260;

Chromatographic condition: column: Phenomenex Gemini NX 5u C18 4.6×150 mm;

Mobile phase: triethylamine solution-acetonitrile-propanol;

Flow rate: 1 mL/min;

Detection wavelength: 280 nm.

The test results are shown in Table 1.

TABLE 1

Results of in-vitro cumulative release degree of sustained-release microparticles and implants

| Sample | 1 d | 2 d | 7 d | 14 d | 21 d | 28 d | 40 d | 50 d | 60 d |
|---|---|---|---|---|---|---|---|---|---|
| Embodiment 1 | 1.19% | 2.27% | 5.98% | 13.30% | 25.45% | 38.50% | 56.32% | 66.80% | 85.45% |
| Embodiment 2 | 1.32% | 2.25% | 4.69% | 11.73% | 21.65% | 32.90% | 51.63% | 63.75% | 82.66% |
| Embodiment 3 | 1.30% | 2.46% | 4.87% | 11.74% | 17.20% | 26.48% | 39.41% | 54.69% | 78.99% |
| Embodiment 4 | 1.05% | 2.00% | 6.36% | 12.11% | 19.28% | 32.61% | 51.82% | 73.69% | 85.20% |
| Embodiment 5 | 0.91% | 1.88% | 7.90% | 16.35% | 29.08% | 45.46% | 69.94% | 83.91% | 94.92% |
| Embodiment 6 | 1.31% | 2.32% | 4.50% | 12.79% | 22.76% | 35.27% | 60.57% | 78.13% | 90.34% |
| Embodiment 7 | 0.90% | 1.95% | 6.80% | 15.86% | 28.19% | 46.35% | 67.81% | 89.61% | 100.00% |
| Embodiment 8 | 1.98% | 3.90% | 8.16% | 16.55% | 29.24% | 49.95% | 78.30% | 90.60% | 99.96% |
| Embodiment 9 | 1.54% | 2.83% | 11.77% | 24.31% | 45.81% | 64.64% | 82.72% | 94.20% | 100.00% |
| Embodiment 10 | 1.89% | 3.18% | 13.40% | 31.05% | 50.12% | 70.00% | 88.65% | 98.50% | 100.00% |
| Embodiment 11 | 1.48% | 2.52% | 14.88% | 28.95% | 47.35% | 64.50% | 82.60% | 93.00% | 100.00% |
| Embodiment 12 | 1.36% | 2.48% | 8.46% | 19.78% | 37.25% | 52.57% | 73.98% | 87.23% | 100.00% |
| Embodiment 13 | 1.60% | 3.15% | 9.80% | 17.81% | 29.25% | 42.57% | 64.69% | 80.64% | 95.70% |
| Embodiment 14 | 1.94% | 3.10% | 13.90% | 28.34% | 43.64% | 68.82% | 85.56% | 99.96% | 100.00% |
| Embodiment 15 | 1.69% | 3.61% | 9.37% | 19.82% | 30.13% | 46.49% | 70.24% | 87.35% | 99.97% |
| Embodiment 16 | 1.81% | 3.89% | 10.42% | 17.87% | 28.02% | 42.37% | 72.26% | 88.00% | 100.00% |
| Embodiment 17 | 0.89% | 1.62% | 7.31% | 16.03% | 28.05% | 40.87% | 60.78% | 78.42% | 89.95% |
| Embodiment 18 | 1.00% | 1.65% | 7.70% | 16.78% | 28.55% | 41.17% | 62.48% | 81.03% | 91.88% |
| Embodiment 19 | 1.85% | 2.55% | 13.70% | 26.25% | 42.83% | 53.66% | 71.50% | 85.00% | 98.10% |
| Embodiment 20 | 1.03% | 1.83% | 8.59% | 16.91% | 28.81% | 40.67% | 62.72% | 80.10% | 92.15% |
| Embodiment 21 | 1.10% | 1.94% | 9.35% | 19.86% | 30.64% | 48.80% | 69.56% | 83.37% | 95.95% |
| Embodiment 22 | 1.32% | 2.15% | 11.60% | 24.68% | 38.00% | 47.67% | 64.34% | 79.21% | 91.05% |
| Embodiment 23 | 1.19% | 1.97% | 10.05% | 22.80% | 31.95% | 40.34% | 63.76% | 81.50% | 93.14% |
| Embodiment 24 | 0.99% | 2.00% | 10.77% | 22.81% | 43.81% | 59.64% | 77.22% | 89.40% | 100.00% |
| Embodiment 25 | 1.18% | 2.28% | 14.60% | 29.55% | 45.00% | 61.26% | 78.14% | 92.26% | 100.00% |

The method for analyzing the particle size of the microparticles prepared in Embodiments 1-23 mentioned above was as follows: dispersing about 10 mg of the microparticles in liquid paraffin, performing ultrasonic dispersion for about 30 s, and measuring by using a Beckman Coulter laser particle size analyzer.

Embodiment 27: Determination of Burst and In-Vitro Release Curves of Microparticles and Implants The sustained-release microparticles and the implant prepared in Embodiments 1-25 mentioned above were subjected to burst release and in-vitro release curve determination, and the determination method was as follows: accurately putting 20 mg of the drug-containing microparticles or implant into a 15 mL centrifuge tube, and by using a pH7.4 PBS buffer (containing 0.02% of sodium azide as a bacteriostatic agent) as a release medium, performing in-vitro release degree determination of the microparticles and implant in a constant-temperature air bath shaker under the conditions of an oscillation speed of 100 rpm and a temperature of 37° C.±0.5° C. All the release medium was removed and supplemented with the same amount of new release medium on 1 d, 2 d, 7 d, 14 d, 21 d, 28 d, 40 d, 50 d and 60 d respectively, and the drug release amount was determined by high performance liquid chromatography. The determination method was as follows:

It can be seen from the in-vitro release results of Table 1 that the sustained-release microparticles prepared by using the solid dispersion of the present invention and the prepared implants have no phenomenon of burst release or obvious delayed release, and the whole release trend is close to zero-order release. Among them, some samples have an in-vitro release period of 40-50 days, some samples have an in-vitro release period of 50-60 days, some samples have an in-vitro release period of more than 60 days, and they have an excellent sustained-release effect.

Embodiment 28

With leuprorelin acetate as a drug and PLGA (molecular weight of 50 kDa, monomer ratio of 50/50, terminal carboxyl group) as a carrier, leuprorelin microspheres were prepared by the methods in Embodiment 1 of US20080131513 and Embodiment 10 of US20020198315A1 respectively. Under same conditions, an in vitro release effect of the leuprorelin microspheres was compared with that of the leuprorelin microspheres in Embodiment 9 of the present invention. Data is as shown in Table 2.

TABLE 2

|  | 1 d | 2 d | 7 d | 14 d | 21 d | 28 d | 40 d | 50 d | 60 d |
|---|---|---|---|---|---|---|---|---|---|
| US20080131513 | 2.09% | 4.20% | 8.77% | 14.54% | 18.72% | 22.69% | 31.42% | 43.10% | 52.88% |
| US20020198315A1 | 7.86% | 12.33% | 15.13% | 18.65% | 20.19% | 36.48% | 73.77% | 98.60% | 100.00% |
| Embodiment 9 | 1.54% | 2.83% | 11.77% | 24.31% | 45.81% | 64.64% | 82.72% | 94.20% | 100.00% |

It can be seen from the data in Table 2 that compared with the leuprorelin microspheres in Embodiment 9 of the present invention, the leuprorelin microspheres prepared by the method in Embodiment 1 of US20080131513 were released more slowly, which may be due to slow PLGA degradation caused by the small change in the microenvironment of the microspheres. A release amount of the leuprorelin microspheres prepared by the method in Embodiment 10 of US20020198315A1 on the first day is about 5 times that of the microspheres in Embodiment 9 of the present invention, which may be caused by more drugs on a surface of the microspheres, but the release is slow in the $2^{nd}$ day to the $14^{th}$ day and rapid in $28^{th}$ day to $35^{th}$ day, indicating that PLGA degradation in the microspheres in the $2^{rd}$ day to the $14^{th}$ day is rapid, an acidic degradation product generated during degradation cannot be discharged, and the PLGA degradation is further accelerated. Therefore, the release of the microspheres is obviously accelerated in the later stage. Compared with US20080131513 and US20020198315A1, the microspheres prepared by the preparation method of the present invention have a more ideal sustained-release behavior.

Embodiment 29

A solid mixture of leuprorelin acetate and PLGA (molecular weight of 50 kDa, monomer ratio of 50/50, terminal carboxyl group) was prepared by the method in U.S. Pat. No. 5,556,642, and the particle size of a polypeptide in the solid mixture was compared with that in the solid dispersion prepared in Embodiment 9 of the present invention by the following method: the solid mixture or the solid dispersion prepared in Embodiment 9 was dissolved in dichloromethane (10% wt), then filtered with filter cloths of 1 μm, 10 μm, 50 μm, 100 μm, 200 μm, and 500 μm, and a recovery rate (%) of leuprorelin in a filtrate was determined. Results are shown in Table 3.

TABLE 3

|  | 1 μm | 10 μm | 50 μm | 100 μm | 200 μm | 500 μm |
|---|---|---|---|---|---|---|
| Solid mixture | 31.24% | 58.34% | 78.92% | 90.11% | 95.64% | 98.08% |
| Solid dispersion in Embodiment 9 | 46.37% | 74.15% | 98.22% | 100% | 100% | 100% |

It can be seen from the data in Table 3 that a mixture of leuprorelin and polymer prepared by the method (solvent evaporation) in U.S. Pat. No. 5,556,642 contains about 10% of leuprorelin particles larger than 100 μm, and the particles are not beneficial for preparing microspheres with a particle size of 20 μm to 100 μm.

Embodiment 30: Needle Passing Ability Test of Microparticles

About 20 mg of the microparticle sample was suspended in 2 mL of diluent (3% carboxymethylcellulose, 0.9% NaCl), then suck into a syringe and respectively injected into commercially available 1 kg-heavy pig hind legs (muscles) through a 24-30 G syringe needle. Each injection was carried out for 20 seconds or less, and the needle passing ability was observed. The results are shown in Table 4.

TABLE 4

Results of needle passing ability test of microparticles

|  | Needle Model | | | |
|---|---|---|---|---|
| Sample Number | 24 G | 26 G | 28 G | 30 G |
| Embodiment 3 (45-85 μm) | ++ | ++ | ++ | ++ |
| Embodiment 6 (20-77 μm) | ++ | ++ | ++ | ++ |
| Embodiment 8 (30-92 μm) | ++ | ++ | ++ | ++ |
| Embodiment 10 (25-110 μm) | ++ | ++ | ++ | + |
| Embodiment 13 (24-130 μm) | ++ | ++ | ++ | + |

Note:
++ very good needle push smoothness, + common needle push smoothness, − retarding, −− blocking.

The results of needle passing ability in Table 4 show that the suspensions of microparticles having different particle sizes prepared by the present invention can be sucked into the syringe through a 30 gauge needle and the contents of the syringe can be completely injected into the pork without retarding or blocking, indicating that the microparticles of the present invention can be administered by subcutaneous or intramuscular injection.

Embodiment 31: Determination of Residual Amounts of Organic Solvents

The residual amounts of the organic solvent A and organic solvent B in the solid dispersions and the organic solvent A and the organic solvent C in the sustained-release microparticles in Embodiments 1-23 of the present invention were determined. The determination methods are well-known determination methods, and are accurate to 0.01%. The test results are shown in Table 5.

TABLE 5

Determination results of residual amounts of organic solvents

|  | Solid Dispersion | | Sustained-release Microparticles | |
|---|---|---|---|---|
|  | Organic Solvent | | | |
| Sample | Organic Solvent A | Organic Solvent B | Organic Solvent A | Organic Solvent C |
| Embodiment 1 | — | — | — | — |
| Embodiment 2 | — | — | — | — |
| Embodiment 3 | 0.01% | — | — | — |
| Embodiment 4 | — | — | — | — |

TABLE 5-continued

Determination results of residual amounts of organic solvents

| | Solid Dispersion Organic Solvent | | Sustained-release Microparticles | |
|---|---|---|---|---|
| Sample | Organic Solvent A | Organic Solvent B | Organic Solvent A | Organic Solvent C |
| Embodiment 5 | — | — | — | — |
| Embodiment 6 | — | — | — | — |
| Embodiment 7 | — | — | — | — |
| Embodiment 8 | — | — | — | — |
| Embodiment 9 | — | — | — | — |
| Embodiment 10 | — | — | — | — |
| Embodiment 11 | — | — | — | — |
| Embodiment 12 | — | — | — | — |
| Embodiment 13 | — | — | — | — |
| Embodiment 14 | — | — | — | — |
| Embodiment 15 | 0.01% | — | — | — |
| Embodiment 16 | — | — | — | — |
| Embodiment 17 | — | — | — | — |
| Embodiment 18 | — | — | — | — |
| Embodiment 19 | — | — | — | — |
| Embodiment 20 | — | — | — | — |
| Embodiment 21 | — | — | — | — |
| Embodiment 22 | — | — | — | — |
| Embodiment 23 | — | — | — | — |

Note:
— indicates undetected or content below the detection limit.

It can be seen from the results of the residual amounts of the organic solvents in Table 5 that in the solid dispersion and the sustained-release microparticles prepared by the present invention, the residual amount of the organic solvent is low, or the organic solvent is undetected, or the residual amount is lower than the detection limit, so there is no side effect caused by the organic solvent to the patient after administration, and it also helps to maintain the stability of the microparticles and prolong the shelf life.

Embodiment 32

A leuprorelin/PLGA (molecular weight of 50 kDa, monomer ratio of 50/50, terminal carboxyl group) solid dispersion was prepared by using glacial acetic acid, glacial acetic acid/ethanol (3:1), and glacial acetic acid/water (3:1) as an organic solvent A, and using anhydrous diethyl ether, hexane, cyclohexane, n-heptane, anhydrous diethyl ether/hexane (volume ratio of 3:1), anhydrous diethyl ether/hexane (volume ratio of 1:1), and anhydrous diethyl ether/hexane (volume ratio 1:3) as an organic solvent B, and a residual amount (%) of acetic acid in the solid dispersion was determined, and was accurate to 0.0001%. Results are shown in Table 6.

TABLE 6

| Organic solvent A | Organic solvent B | Residual amount of acetic acid |
|---|---|---|
| Glacial acetic acid | Anhydrous diethyl ether | 0.0007% |
| Glacial acetic acid | Hexane | 0.0084% |
| Glacial acetic acid | Cyclohexane | 0.0099% |
| Glacial acetic acid | N-heptane | 0.0072% |
| Glacial acetic acid | Anhydrous diethyl ether/hexane (volume ratio of 3:1) | 0.0015% |
| Glacial acetic acid | Anhydrous diethyl ether/hexane (volume ratio of 1:1) | 0.0038% |
| Glacial acetic acid | Anhydrous diethyl ether/hexane (volume ratio of 1:3) | 0.0055% |
| Glacial acetic acid/ethanol (3:1) | Anhydrous diethyl ether | 0.0078% |
| Glacial acetic acid/water (3:1) | Anhydrous diethyl ether | / |

It can be seen from the above results that when the glacial acetic acid is used as the organic solvent A, residual amounts of the acetic acid in the leuprorelin solid dispersion in different organic solvents B are all lower than 0.01%, wherein the anhydrous diethyl ether has a best effect. When the anhydrous diethyl ether is used as the organic solvent B, different organic solvents A have obvious differences. When the glacial acetic acid/ethanol (3:1) is used as the solvent, a solubility of PLGA is decreased, and a solid content can only reach 89% of the glacial acetic acid. When the glacial acetic acid/water (3:1) is used as the solvent, the solubility of the PLGA is decreased significantly, and the solid content can only reach 72% of the glacial acetic acid. Moreover, the solid dispersion cannot be prepared by dropping the glacial acetic acid/water (3:1) in the anhydrous diethyl ether, and a product is semi-gel, which is caused by an incompatibility between the water and the anhydrous diethyl ether, so that the water is still wrapped in the polymer matrix. Therefore, using the glacial acetic acid as the organic solvent A and using the anhydrous diethyl ether as the organic solvent B is the best choice.

Embodiment 33: Animal Testing 40 healthy male Sprague-Dawley rats, weighing 250±20 g, were randomly divided into the drug-administered groups (4 groups) and the blank group (1 group), each group consisting of 8 rats. The rats in the drug-administered groups were injected subcutaneously with the goserelin microparticles of Embodiment 6, the leuprorelin microparticles of Embodiment 7, the triptorelin microparticles of Embodiment 8 and the buserelin microparticles of Embodiment 12 respectively, and the microparticles were suspended with a diluent containing 3% carboxymethylcellulose and 0.9% NaCl. The dose to each of the rats in the drug-administered groups was 200 μg/kg, and the blank group was subcutaneously injected with the same volume of normal saline. Blood was taken from the tail vein at the same time on 0 d, 0.5 d, 1 d, 2 d, 3 d, 4 d, 5 d, 6 d, 7 d, 14 d, 21 d, 28 d, 35 d, 42 d, 49 d, 56 d, 63 d and 70 d after administration, the concentration of testosterone in serum was determined by radioimmunoassay, and then the serum testosterone concentration-time curve graph was made. The results are shown in FIG.

As can be seen from the graph of FIG., the goserelin microparticles of Embodiment 6, the leuprorelin microparticles of Embodiment 7, the triptorelin microparticles of Embodiment 8 and the buserelin microparticles of Embodiment 12 of the present invention can well control the serum testosterone concentration within 70 days after administration, and the serum testosterone concentration is less than 5 ng/mL within 4-63 days after administration, and the serum testosterone concentration within 7-50 days is less than about 4 ng/mL, which is significantly lower than the blank group, indicating that the goserelin microparticles, leuprorelin microparticles, triptorelin microparticles and buserelin microparticles of the present invention can release the active drug for a long time and achieve the desired treatment effect after administration, can reduce the frequency of administration and helps to improve patient compliance.

Finally, it should be noted that the above embodiments are only used to illustrate the technical solutions of the present invention and are not intended to limit the protection scope of the present invention. Although the present invention has been described in detail with reference to the preferred embodiments, a person skilled in the art should understand that the technical solutions of the present invention may be modified or equivalently substituted without departing from the spirit and scope of the technical solutions of the present invention.

What is claimed is:

1. A method for preparing sustained-release microparticles comprising the following steps:
   1) Preparing a solid dispersion of a water-soluble drug and a biodegradable and biocompatible poorly water-soluble polymer; the water-soluble drug is selected from the group consisting of goserelin, triptorelin, leuprorelin and octreotide; the biodegradable and biocompatible poorly water-soluble polymer is PLGA, wherein a ratio of the water-soluble drug to the PLGA is 1:1-99 by weight;
   2) dissolving the solid dispersion prepared in step 1) in an organic solvent C to form a solid dispersion emulsion, the organic solvent C is dichloromethane;
   3) adding the solid dispersion emulsion obtained in step 2) into a surfactant-containing aqueous solution to form a uniform emulsion; and
   4) solidifying microparticles in the emulsion by solvent volatilization or solvent extraction, collecting the microparticles, washing with ultrapure water several times to remove the surfactant attached to the surface of the microparticles, and drying to obtain the sustained-release microparticles without trace of the organic solvent A and C, 100% of the water-soluble drug in the sustained-release microparticles is released in 60 days close to zero order release kinetics, wherein diameters of the microparticles are between 20 and 100 μm;

wherein, step 1) is carried out by the following steps:
   11) completely dissolving the biodegradable and biocompatible poorly water-soluble polymer and the water-soluble drug in an organic solvent A to form a mixed solution of the drug and the polymer; and
   12) adding the mixed solution into an organic solvent B or adding the organic solution B into the mixed solution to produce a precipitate, collecting the precipitate, washing the precipitate with the organic solvent B several times, and removing the organic solvent B to obtain a solid dispersion of the water-soluble drug and the poorly water-soluble polymer, wherein the organic solvent B is incapable of dissolving the poorly water-soluble polymer and the water-soluble drug, organic solvent A is glacial acetic acid; and the organic solvent B is anhydrous diethyl ether.

2. The method according to claim 1, characterized in that the method further comprises the step of adding an additive which is added during the process of preparing the solid dispersion in step 1) or during the process of preparing the solid dispersion emulsion in step 2); and the additive is 0.01-10% of the sum of the mass of the water-soluble drug and the poorly water-soluble polymer.

* * * * *